US010030263B1

(12) United States Patent
Wang et al.

(10) Patent No.: US 10,030,263 B1
(45) Date of Patent: Jul. 24, 2018

(54) MULTIPLEXED RNA QPCR ASSAY

(71) Applicants: Jia-Wang Wang, Tampa, FL (US); Richard F. Lockey, Tampa, FL (US)

(72) Inventors: Jia-Wang Wang, Tampa, FL (US); Richard F. Lockey, Tampa, FL (US)

(73) Assignee: University of South Florida, Tampa, FL (US)

( * ) Notice: Subject to any disclaimer, the term of this patent is extended or adjusted under 35 U.S.C. 154(b) by 182 days.

(21) Appl. No.: 14/833,588

(22) Filed: Aug. 24, 2015

Related U.S. Application Data

(60) Provisional application No. 62/041,391, filed on Aug. 25, 2014.

(51) Int. Cl.
*C12Q 1/686* (2018.01)

(52) U.S. Cl.
CPC .................................... *C12Q 1/686* (2013.01)

(58) Field of Classification Search
CPC ............ C12Q 1/6851; C12Q 2521/107; C12Q 2525/173; C12Q 2525/301; C12N 2310/141; C12N 2320/10
USPC ......................................................... 435/91.2
See application file for complete search history.

(56) References Cited

U.S. PATENT DOCUMENTS 8,048,626 B2 11/2011 Hassibi et al.
2013/0045885 A1* 2/2013 Mohapatra ........... C12Q 1/6851 506/9
2015/0322510 A1* 11/2015 Higuchi ............... C12Q 1/6853 506/9

FOREIGN PATENT DOCUMENTS

WO WO 2007054520 5/2007
WO WO 2010075413 7/2010
WO WO 2012047297 A2 4/2012
WO WO 2013079606 A1 6/2013

OTHER PUBLICATIONS

Benes and Castoldi. Methods, vol. 50, pp. 244-249, Jan. 2010.*
Turner et al ., Plant Signaling and Behavior, vol. 8, No. 8, e24918, pp. 1-4, Aug. 2013.*

* cited by examiner

*Primary Examiner* — Cynthia B Wilder
(74) *Attorney, Agent, or Firm* — Thomas|Horstemeyer, LLP

(57) ABSTRACT

Described herein are multiplexed RNA, including miRNA, PCR-based assays.

11 Claims, 11 Drawing Sheets

| cDNA mixture | RT primer | miRNA | Detected | Un-detected |
|---|---|---|---|---|
| miR-142, miR-150 and Let-7a | FAM-RT primer | Biotin-miR-150 | miR-150 | miR-142, and Let-7a |
| miR-142, miR-150 and Let-7a | VIC-RT primer | Biotin-Let-7a | Let-7a | miR-142, and miR-150 |

FIG. 10

SEQUENCE LISTING

<160> NUMBER OF SEQ ID NOS: 29

<210> SEQ ID NO 1
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (73)..(73)
<223> OTHER INFORMATION: n is a, c, g, or t

<400> SEQUENCE: 1
gcctctgact ccaggatctg tagacactcg aagatcgcat aggtctggca cagttttttt      60
tttttttttt tvn                                                         73

<210> SEQ ID NO 2
<211> LENGTH: 22
<212> TYPE: DNA
<213> ORGANISM: Artificial Sequence
<220> FEATURE:
<223> OTHER INFORMATION: probe

<400> SEQUENCE: 2
ctgtgccaga cctatgcgat ct                                               22

<210> SEQ ID NO 3
<211> LENGTH: 73
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (73)..(73)
<223> OTHER INFORMATION: n is a, c, g, or t

<400> SEQUENCE: 3
gcctctgact ccaggatctg tagacgtcgg gactcgattg tgtatgctgc gtgttttttt      60
tttttttttt tvn                                                         73

-continued

<210> SEQ ID NO 4
<211> LENGTH: 24
<212> TYPE: DNA
<213> ORGANISM: Artificial Sequence
<220> FEATURE:
<223> OTHER INFORMATION: probe

<400> SEQUENCE: 4
cacgcagcat acacaatcga gtcc 24

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
gcctctgact ccaggatctg tagac 25

<210> SEQ ID NO 6
<211> LENGTH: 27
<212> TYPE: DNA
<213> ORGANISM: Artificial Sequence
<220> FEATURE:
<223> OTHER INFORMATION: cDNA

<400> SEQUENCE: 6
cctctcccaa cccttgtacc agtgaaa 27

<210> SEQ ID NO 7
<211> LENGTH: 40
<212> TYPE: DNA
<213> ORGANISM: Artificial Sequence
<220> FEATURE:
<223> OTHER INFORMATION: cDNA

<400> SEQUENCE: 7
ggttggagta acacttgagg tagtaggttg tatagttaaa 40

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
cctctcccaa cccttgtacc agtgaaa 27

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9
ggttggagta acacttgagg tagtaggttg tatagttaaa 40

<210> SEQ ID NO 10
<211> LENGTH: 40
<212> TYPE: DNA
<213> ORGANISM: Artificial Sequence
<220> FEATURE:
<223> OTHER INFORMATION: primer

<400> SEQUENCE: 10
cgtcatagca tcattgtagt gtttcctact ttatggaaaa 40

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
tcccagtaaa ggctgggctg agaaaa 26

<210> SEQ ID NO 12
<211> LENGTH: 37
<212> TYPE: DNA
<213> ORGANISM: Artificial Sequence
<220> FEATURE:
<223> OTHER INFORMATION: primer

<400> SEQUENCE: 12
caagttagaa gtaccctgta gatccgaatt tgtgaaa 37

<210> SEQ ID NO 13
<211> LENGTH: 34
<212> TYPE: DNA
<213> ORGANISM: Artificial Sequence
<220> FEATURE:
<223> OTHER INFORMATION: primer

<400> SEQUENCE: 13
caacttgtct gaggtagtag gttgtgtggt taaa 34

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
accttgggtg aggtaggagg ttgtatagtt aaa 33

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
ggtggagcct gaggtagtag tttgtacagt taaa 34

<210> SEQ ID NO 16
<211> LENGTH: 31
<212> TYPE: DNA
<213> ORGANISM: Artificial Sequence
<220> FEATURE:
<223> OTHER INFORMATION: primer

<400> SEQUENCE: 16
cgtcatgcat gggtgtatag ttgagtgcaa a 31

<210> SEQ ID NO 17
<211> LENGTH: 41

-continued

<212> TYPE: DNA
<213> ORGANISM: Artificial Sequence
<220> FEATURE:
<223> OTHER INFORMATION: primer

<400> SEQUENCE: 17
cctcttagtg cactggtgga atgtaaagaa gtatgtataa a 41

<210> SEQ ID NO 18
<211> LENGTH: 38
<212> TYPE: DNA
<213> ORGANISM: Artificial Sequence
<220> FEATURE:
<223> OTHER INFORMATION: primer

<400> SEQUENCE: 18
ggtcgacttc ccattagatg aggtagtagt tagaaaaa 38

<210> SEQ ID NO 19
<211> LENGTH: 35
<212> TYPE: DNA
<213> ORGANISM: Artificial Sequence
<220> FEATURE:
<223> OTHER INFORMATION: primer

<400> SEQUENCE: 19
catcagtcct gggtacataa agaagtatgt gcaaa 35

<210> SEQ ID NO 20
<211> LENGTH: 34
<212> TYPE: DNA
<213> ORGANISM: Artificial Sequence
<220> FEATURE:
<223> OTHER INFORMATION: primer

<400> SEQUENCE: 20
cacattgatt ggaatgtaag gaagtgtgtg gaaa 34

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
ggttcaaccc gtagatccga acttgtgaaa 30

<210> SEQ ID NO 22
<211> LENGTH: 31
<212> TYPE: DNA
<213> ORGANISM: Artificial Sequence
<220> FEATURE:
<223> OTHER INFORMATION: primer

<400> SEQUENCE: 22
cctcctaacc cgtagatccg atcttgtgaa a 31

<210> SEQ ID NO 23
<211> LENGTH: 37
<212> TYPE: DNA
<213> ORGANISM: Artificial Sequence
<220> FEATURE:
<223> OTHER INFORMATION: primer

<400> SEQUENCE: 23

-continued caagttagaa gtaccctgta gatccgaatt tgtgaaa 37

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
actcgacaga gtgtgtgtgt ctgtgtaaa 29

<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25
ggcgaagcct tgtgtgtaca tgtacatgta taaa 34

<210> SEQ ID NO 26
<211> LENGTH: 15
<212> TYPE: DNA
<213> ORGANISM: Artificial Sequence
<220> FEATURE:
<223> OTHER INFORMATION: UQ-mmu-let-7a

<400> SEQUENCE: 26
ggttggagta acact 15

<210> SEQ ID NO 27
<211> LENGTH: 22
<212> TYPE: DNA
<213> ORGANISM: Artificial Sequence
<220> FEATURE:
<223> OTHER INFORMATION: mmu-let-7a

<400> SEQUENCE: 27
tgaggtagta ggttgtatag tt 22

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
gcccggccgg gtgtcgaaa 19

<210> SEQ ID NO 29
<211> LENGTH: 21
<212> TYPE: RNA
<213> ORGANISM: Artificial Sequence
<220> FEATURE:
<223> OTHER INFORMATION: mmu-miR-718

<400> SEQUENCE: 29
cuuccgcccg gccggguguc g 21

MULTIPLEXED RNA QPCR ASSAY

CROSS REFERENCE TO RELATED APPLICATIONS

This application claims the benefit of U.S. Provisional Application Ser. No. 62/041,391 filed on Aug. 25, 2014, having the title “Multiplexed RNA qPCR Assay”, the entirety of which is incorporated herein by reference.

SEQUENCE LISTING

This application contains a sequence listing filed in electronic form as an ASCII.txt file entitled 02259312.txt, created on Aug. 19, 2015, and having a size of 2200 bytes. The content of the sequence listing is incorporated herein in its entirety.

BACKGROUND

MicroRNA (miRNA) is a single strand of ~21-23 ribonucleotides. There are at least 2578 known human mature miRNAs (miRbase, release 20: June 2013). miRNA can regulate targeted mRNA by down-regulating mRNA levels and/or repressing translation. Thus, miRNA has greatly influenced on the field of biomedical research and diagnostics. miRNAs can function in the cell that produces them and/or be secreted into the bloodstream and function in a remote cell. As miRNAs regulate gene expression, typically their levels are tightly controlled. Deregulation of miRNAs is therefore implicated in the etiology and pathology of many diseases and disorders. Therefore, miRNAs can be used as robust biomarkers for disease diagnosis, especially for early diagnosis, staging, prognosis, and to evaluate a response in a subject to therapy or treatment.

Given at least the small size of miRNAs, they have proven difficult to accurately and quantitatively detect, which limits their usefulness in disease diagnostics. As such, there exists a need for improved miRNA detection methods for use at least in research and biomedical diagnostics.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 6B shows the correlation between the PCR reactions performed with the FAM oligo-probe and those performed with the VIC oligo-probe.

FIG. 10 demonstrates exemplary specific combinations of primers, synthetic miRNAs, and oligo-probes used to determine the specificity of the universal multiplexed cDNA assay.

DETAILED DESCRIPTION

Figure 1:
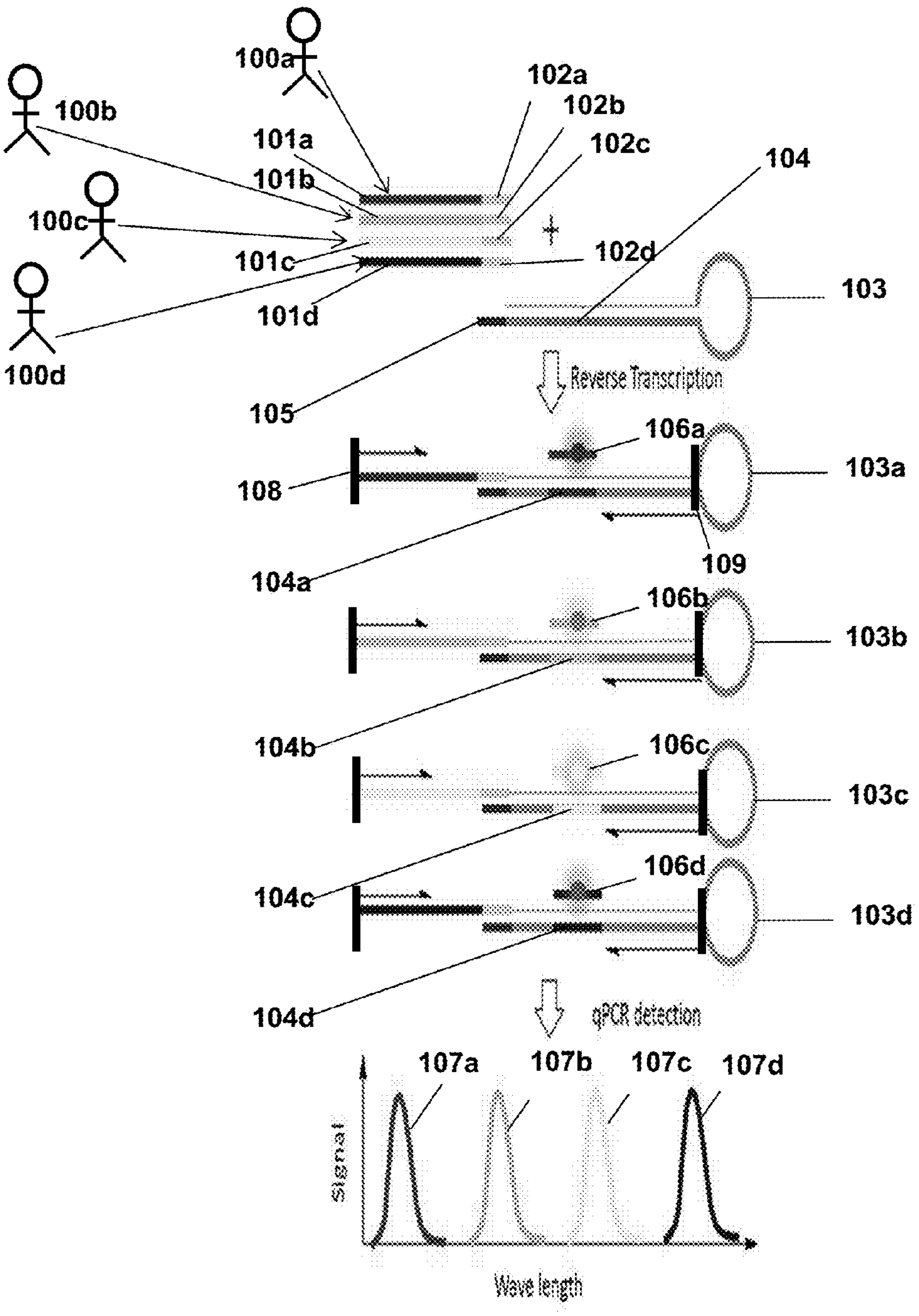
FIG. 1 shows one embodiment of a universal multiplexed qPCR assay for detecting RNA molecules, particularly miRNA and mRNA, in a sample.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, the term "oligo" refers to a nucleotide ranging from 10 to about 50 nucleotides in length.

As used herein, the term "poly-A" refers to a nucleotide sequence that contains only adenosine nucleotides and ranges in length from about 10 to about 50 nucleotides.

As used herein, "hybridization" refers to a reaction in which one or more polynucleotides react to form a complex that is stabilized via hydrogen bonding between a particular purine and a particular pyrimidine in double stranded nucleic acid molecules (DNA-DNA, DNA-RNA, RNA-RNA, cDNA-DNA, cRNA-DNA, cRNA-RNA). Various degrees of stringency of hybridization can be employed. The more stringent the conditions, the greater the complementarity that is required duplex formation. Stringency of the hybridization conditions can be controlled by temperature, probe concentration, primer concentration, ionic strength, time, and the like.

As used herein "melting temperature (Tm)" refers to the temperature at which one-half of a particular nucleotide duplex (DNA-DNA, DNA-RNA, RNA-RNA, cDNA-DNA, cRNA-DNA, cRNA-RNA) will dissociate and become single stranded. Calculations for estimating Tm are Well-known in the art. For example, the melting temperature may be described by the following formula (Beltz, G. A., K. A. Jacobs, T. H. Eickbush, P. T. Cherbas, and F. C. Kafatos, Methods of Enzymology, R. Wu, L. Grossman and K. Moldave [eds.] Academic Press, New York 100:266-285, 1983). Tm=81.5° C.+16.6 Log [Na+]+0.41(% G+C)-0.61(% formamide)-600/length of duplex in base pairs. A more accurate estimation of Tm may be obtained using nearest-neighbor models. Breslauer, et al., Proc. Natl. Acad. Sci. USA, 83(11): 3746-3750 (1986); SantaLucia, Proc. Natl Acad. Sci. USA, 95: 1460-1465 (1998); Allawi & Santa Lucia, Biochemistry 36(34): 10581-94 (1997); Sugimoto et al., Nucleic Acids Res., 2414501-4505 (1996). Tm may also be routinely measured by differential scanning calorimetry (Duguid et al., Biophys J, 71(6): 3350-60, 1996) in a chosen solution, or by other methods known in the art, such as UV-monitored melting. As the stringency of the hybridization conditions is increased, higher degrees of homology are obtained.

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "isolated" refers to separation from constituents, cellular and otherwise, with which a polynucleotide, peptide, polypeptide, protein, antibody, or fragments thereof, are normally associated in nature. A non-naturally occurring polynucleotide, peptide, polypeptide, protein, antibody, or fragments thereof, does not require "isolation" to distinguish it from its naturally occurring counterpart.

As used herein, "diluted" used in reference to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "specific binding", "specific hybridization", and the like refer to binding which occurs between such paired species as nucleotide/nucleotide, enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "control" is an alternative subject or sample used in an experiment for comparison purposes and included to minimize or distinguish the effect of variables other than an independent variable.

As used herein, "positive control" refers to a "control" that is designed to produce the desired result, provided that all reagents are functioning properly and that the experiment is properly conducted.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "separated" refers to the state of being physically divided from the original source or population such that the separated compound, agent, particle, or molecule can no longer be considered part of the original source or population.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "purified" is used in reference to a nucleic acid sequence, peptide, or polypeptide or other compound that has increased purity relative to the natural environment.

As used herein, "polypeptides" or "proteins" are as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" refers to a hereditary unit corresponding to a sequence of DNA that occupies a specific location on a chromosome and that contains the genetic instruction for a characteristic(s) or trait(s) in an organism.

As used herein, "deoxyribonucleic acid (DNA)" and "ribonucleic acid (RNA)" generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), microRNA (miRNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "microRNA" refers to a small non-coding RNA molecule containing about 21 to about 23 nucleotides found in organisms, which functions in transcriptional and post-transcriptional regulation of transcription and translation of RNA.

Discussion

To study and use microRNA (miRNA) and messenger RNA (mRNA), it is desirable to specifically and sensitively detect and quantify miRNA and mRNA molecules. Northern hybridization, cloning, microarray techniques have all been used for both mRNA and miRNA analysis. However, these techniques lack the sensitivity and/or specificity to meet research and diagnostic demands. In the past decade, techniques based on the quantitative polymerase chain reaction (qPCR) have been employed to improve mRNA and miRNA analysis. However, current procedures using the aforementioned techniques, especially qPCR, are time consuming and expensive. In the vast majority of situations, it is desired to analyze hundreds, if not thousands, of samples for multiple miRNA or mRNA molecules at a time. Thus, it can be appreciated that with type of sample size, expenses of both time and money limit the size of samples that can be feasibly analyzed.

Current qPCR procedures are inadequate largely due to the inability to feasibly multiplex reactions. In other words, current qPCR methods lack universal detection, because different individual reverse transcription primers, probes, forward and reverse PCR primers have to be used to detect different miRNAs and mRNAs. Further, it is often desirable to analyze both miRNA and mRNA simultaneously in the same sample. In order for multiplexing to occur, many factors must be optimized in order to minimize variation between samples or molecules analyzed, between different wells in qPCR plates, and between different qPCR plates used, so as to make comparisons between samples possible. Variation and assay sensitivity are positively correlated. Current attempts at developing multiplexed miRNA and or mRNA assays have not been able to reduce variation sufficiently so as to achieve adequate sensitivity.

mRNA and miRNA are structurally different, which creates a barrier to development of a universal multiplexing qPCR assay that can simultaneously detect both mRNA and miRNA. For example, the melting temperature (Tm) and GC content of both miRNA and mRNA can vary greatly between one another and between different molecules of miRNA or mRNA. If these factors are not addressed, variation is too great and sensitive is lost. Current techniques do not reduce variation, in part due to an inability to account for the structural differences between miRNA and mRNA, to allow for a universal multiplexing reaction that can detect both miRNA and mRNA from one or more samples.

With the shortcomings of current techniques in mind, provided herein are methods, reagents, assays, and kits, that allow for high-throughput and simultaneous detection of one or more miRNA species and/or one or more mRNA species from one or more samples. In an embodiment miRNA or mRNA from one or more subjects is polyadenylated in individual reactions. Almost all mRNAs are naturally polyadenylated and thus the polyadenylation is not required for those mRNAs. After polyadenylation, cDNA is generated by reverse transcribing the polyadenylated miRNA or mRNA using a universal reverse transcription (RT) stem-loop adapter primer. The cDNA produced from the two or more individual polyadenylation and RT procedures are combined into one polymerase chain reaction (PCR) (such as a real-time quantitative PCR (qPCR)) reaction along with RT stem-loop adapter primer specific oligo-probe and target-specific forward primers, where all the target-specific forward primers all have a melting temperature (Tm) of between 65° C. and 75° C.±2° C.

Figure 4:
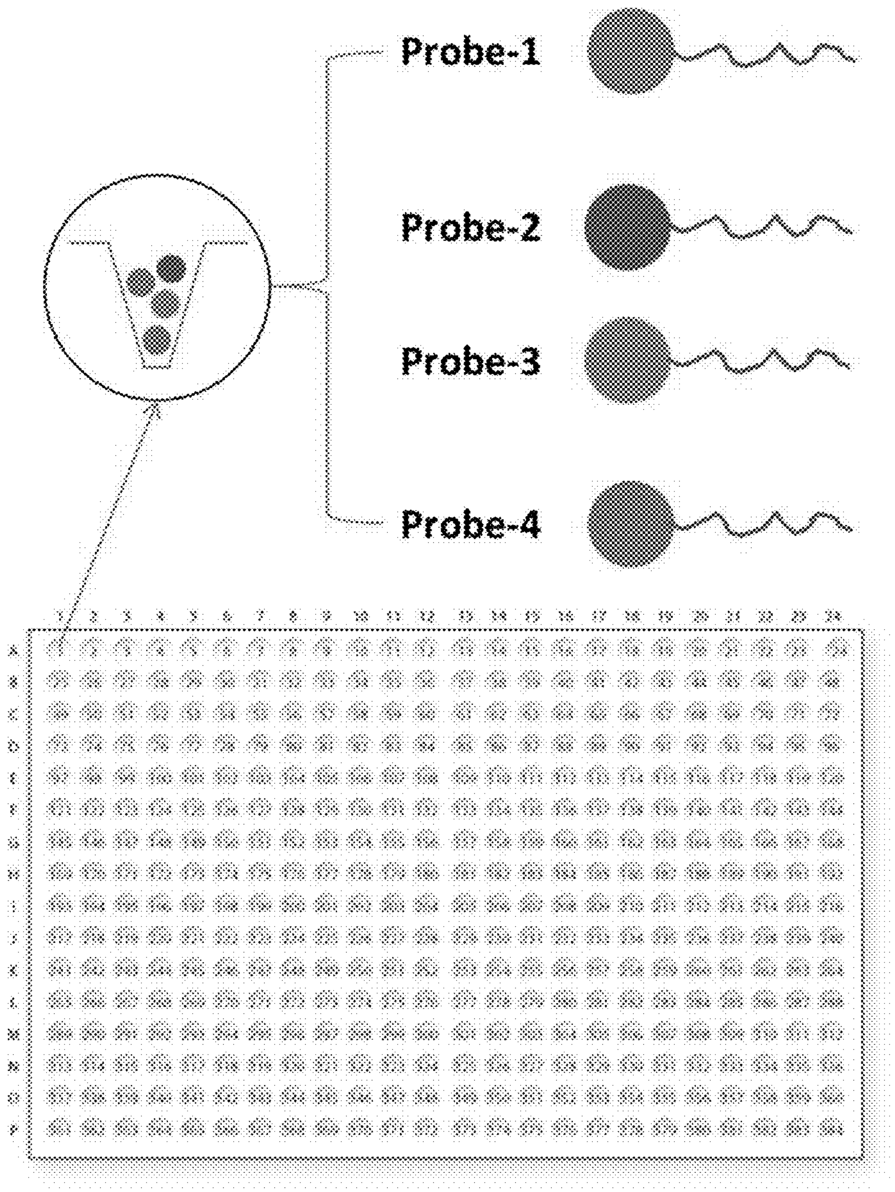
FIG. 4, shows generally a high-throughput multiplexed qPCR reaction.

In short, the assay allows one reaction qPCR (e.g. as contained in one well of a reaction plate) to simultaneously analyze at least four different target sequences (e.g. gene sequences or miRNA sequences) from a source, or to analyze one target sequence from miRNA and or mRNA from four different sources in a single reaction. This is generally illustrated in FIG. 4. Up to four PCR reactions can be conducted in one well so that 1536 different miRNAs or mRNA can or different samples be detected in one 384 well plate. It is especially useful to compare the differential expression of miRNAs in paired samples such as normal and diseased tissues, as experimental variations in qPCR reaction is eliminated, allowing sensitive detection of expression difference of miRNA or mRNA. In addition to increasing the specificity over current techniques, the embodiments described herein provide a less expensive and less time-consuming assay for mRNA and/or miRNA detection. Moreover, the embodiments described herein decrease variation within the assay, thus improving sensitivity of mRNA and/or miRNA detection over current techniques. The assay, in a single reaction, can specifically detect, quantify, and/or profile as little as about one molecule of a mRNA or miRNA while simultaneously detecting, quantifying, and/or profiling as little as about one molecule of one or more additional mRNA or miRNA molecules.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Assays

With the general description of the embodiments in mind, discussion begins with FIG. 1, which illustrates one embodiment of a multiplexed miRNA and/or mRNA detection assay. For illustrative purposes, in FIG. 1 miRNA/mRNA molecules labeled 101*a* are derived from subject A 100*a*, miRNA/mRNA molecules labeled 100*b* are derived from subject B 100*b*, miRNA/mRNA molecules labeled 101*c* are derived from subject C 100*c*, and miRNA/mRNA molecules labeled 101*d* are derived from subject D 100*d*. In other words, miRNA/mRNA 101*a* represents all the isolated miRNA/mRNA molecules from subject A 100*a*. Similarly miRNA/mRNA 101*b*, 101*c*, and 101*d* are isolated from subjects B 100*b*, C 100*c*, and subject D 100*d*, respectively. It will be appreciated that while only 4 subjects are shown being analyzed in FIG. 1, as many subjects as the assay will allow for can be analyzed simultaneously.

The method can begin by polyadenylating isolated miRNA and/or mRNA molecules 101*a*, 101*b*, 101*c*, and 101*d* (collectively 101) from 4 different subjects 101*a*, 101*b*, 101*c* and 101*d* (collectively 101). Polyadenylation can occur by contacting the miRNA and/or mRNA molecules 101 with an effective amount of poly(A)polymerase molecules to yield 3' end-polyadenylated mRNA and/or miRNA molecules 102*a*, 102*b*, 102*c*, and 102*d* (collectively 102).

At this point in the method, miRNA/mRNA molecules 101*a* can be processed separately from miRNA/mRNA molecules 101*b*, miRNA/mRNA molecules 101*c*, and miRNA/mRNA molecules 101*d*. miRNA/mRNA molecules 101*b*, can be processed separately from miRNA/mRNA molecules 101*a*, miRNA/mRNA molecules 101*c*, miRNA/mRNA molecules 101*d*. miRNA/mRNA molecules 101*c* can be processed separately from miRNA/mRNA molecules 101*a*, miRNA/mRNA molecules 101*b*, and miRNA/mRNA molecules 101*d*. Finally, miRNA/mRNA molecules 101*d* can be processed separately from miRNA/mRNA molecules 101*a*, miRNA/mRNA molecules 101*b*, and miRNA/mRNA molecules 101*c*. For example, each subject's miRNA/mRNA molecules are processed in different containers (e.g. microfuge tubes).

After polyadenylation, any mRNA not already polyadenylated and miRNA molecules contain a 3' poly-A tail. The poly-A tail can facilitate hybridization to a reverse transcription (RT) stem-loop adapter primer 103, which can contain an oligo-dT region 105. The stem-loop adapter primer 103 can also contain an oligo-probe hybridization sequence 104. The oligo-probe hybridization sequence 104 is unique as to oligo-probe 106*a*, 106*b*, 106*c*, 106*d* (collectively 106) being hybridized.

As shown in FIG. 1, the oligo-probe hybridization sequence 104*a* in RT stem-loop primer 103*a* is specific to oligo-probe 106*a* but not specific to oligo-probe 106*b*, 106*c*, or 106*d*. Similarly, the oligo-probe hybridization sequence 104*b* in RT stem-loop primer 103*b* is specific to oligo-probe 106*b* but, not to oligo-probe 106*a*, 106*c*, or 106*d*. In the same way, the oligo hybridization sequence in the RT stem-loop primer 103*c* and 103*d* are likewise specific for oligo-probes 106*c* and 106*d*, respectively. Each different oligo-probe 106 contains a different quenched probe molecule, as described below. This can allow for detection of mRNA/miRNA from different subjects in the same qPCR reaction as described below.

The oligo-probe 106 can contain an oligo of about 15 to about 50 nucleotides length and can be complimentary to an oligo-probe hybridization sequence 105 within a stem-loop adapter primer 103. The oligo can be operatively bound to a quenched probe molecule. Suitable probe molecules include, but are not limited to, BioSearch blue, acridine, coumarin, FAM, rhodamine green, TET, VIC, JOE, CAL Flour Gold 450, HEX, CAL Flour Orange 560, Quasar 570, TAMRA, rhodamine Red, CAL Flour 590, Cy3.5, CAL Flour Red 610, CAL Fluor Red 635, Pulsar 650, Quasar 670, Quasar 705, Texas Red, LC Red 640, Cy5, and Cy5.5.

Next, a RT reaction for each polyadenylated miRNA/mRNA sample can be completed and cDNA formed. Within the RT reaction for each polyadenylated miRNA/mRNA sample, a different universal reverse stem-loop adapter primer, 103*a*, 103*b*, 103*c*, or 103*d* can be used. As stated above, each universal reverse stem-loop adapter primer is specific for a particular oligo-probe, and therefore each miRNA/mRNA molecule prepared in a particular RT reaction can be detected by the oligo-probe that hybridizes with the universal reverse stem-loop adapter primer during a subsequent qPCR reaction. RT can be performed by contacting the mRNA and/or miRNA template molecule with reverse transcriptase in the presence of the RT stem-loop adapter primer 103.

Next, the cDNA prepared from the samples of miRNA/mRNA 101 from the different subjects 100 can be combined in a single qPCR reaction. This is illustrated in FIG. 4. The qPCR reaction is designed to amplify the region shown that exists between the heavy bolded lines 108, 109. For sake of clarity, only the heavy bolded lines 108, 109 are identified in cDNA produced from subject A 100*a*. However, the same general region is amplified in cDNA from subjects B 100*b*, C 100*c*, and D 100*d*. Also included in the qPCR reaction can be a target-specific forward primer and a universal reverse primer that can hybridize to a region within the adapter primer sequence that lies in a region that can result in amplification of the oligo-probe hybridization sequence when used with the target-specific forward primer. The reverse primer can hybridize with any RT stem-loop adapter primer used regardless of the oligo-probe hybridization sequence contained within.

For a multiplexed high-throughput assay, it can be desirable to achieve homogeneous amplification during qPCR, in which every amplicon is amplified at the same efficiency. Although many factors are important to achieving homogeneous amplification, the melting temperature (Tm) and the GC content of the cDNA templates, two important parameters in PCR amplification that greatly affect the amplification efficiency. In the human genome, the predicted miRNA Tm values range from about 48° C. to about 86° C., with an average of about 66° C. and the miRNA GC percentages range from about 9% to about 95%, with a mean of about 51%. As such, if using miRNA sequences as the forward primers for use in the qPCR reaction and considering the fact that miRNA itself is about the size of a primer used during qPCR amplification, one of ordinary skill in the art will appreciate that it is impossible to homogenously amplify all miRNAs under the same PCR conditions, which is needed for a multiplexed high-throughput assay. For example, using the same amount of starting miRNA templates, RT-qPCR results show that the relative levels of miRNA could be over about 200 times different solely due to differences in amplification efficiency of each different miRNA molecule.

In some embodiments, the target-specific forward qPCR primers can be designed in a way such that the Tm of all the forward target-specific primers within a single reaction each have a Tm of within ±2° C. or less, preferably ±1° C., of a target melting temperature. In some embodiments, the target melting temperature can be about 65° C.–75° C., preferably about 67° C.-72° C. In an embodiment, the target melting temperature can be 70° C. In some embodiments, the Tm of a forward qPCR primer can be adjusted by adding an extra nucleotide sequence. The extra nucleotide sequence can be an artificial sequence that does not form hairpin structure with the sequence it is attached to, does not have homology with the known mature and pre-miRNA sequence(s), and can contain a stretch of more than four guanosine nucleotides. In one non limiting example, UQ-mmu-let-7a has the extra nucleotide sequence: SEQ ID NO: 26: 5' GGTTGGAGTAACACT 3', which can be added, for example, to the mmu-let-7a: TGAGGTAGTAGGTTGTATAGTT (SEQ ID NO.: 27) (See also Table 1). In some embodiments, the extra sequence is added at the 5' end of the primers used to detect miRNAs that have a lower Tm values than 70° C. In other embodiments, the Tm of a target-specific forward qPCR primer is adjusted by truncating the 5' end of those miRNAs that have higher than 70° C. In one non-limiting example, the UQ-mmu-miR-718 primer (GCCCGGCCGGGTGTCGAAA) (SEQ ID NO.: 28) can be truncated from mmu-miR-718, CUUCCGCCCGGCCGGGUGUCG (SEQ ID NO.: 29) (the underlined sequence is removed).

TABLE 1

| Name | Sequence | Usage |
| --- | --- | --- |
| MGB8RT | GCCTCTGACTCCAGGATCTGTAGACACTCGA AGATCGCATAGGTCTGGCACAGTTTTTTTTTTTTTTTTTTVN (SEQ ID NO.: 1) | Universal reverse primer |
| MGB8 | FAM-CTGTGCCAGACCTATGCGATCT-MGBNFQ (SEQ ID NO.: 2) | MGB probe for MGB8RT |
| MGB12RT | GCCTCTGACTCCAGGATCTGTAGACGTCG GGACTCGATTGTGTATGCTGCGTGTTTTTTTTTTTTTTTTTTVN (SEQ ID NO.: 3) | Universal reverse primer |
| MGB12 | VIC-CACGCAGCATACACAATCGAGTCC-MGBNFQ (SEQ ID NO.: 4) | MGB probe for MGB12RT |
| URPN | GCCTCTGACTCCAGGATCTGTAGAC (SEQ ID NO.: 5) | Universal reverse primer |
| miR150biotin | /5Biosg/CCTCTCCCAACCCTTGTACCAGTGAAA (SEQ ID NO.: 6) | Pull down miR150 cDNA |
| Let7abiotin | /5Biosg/GGTTGGAGTAACACTTGAGGTAGTAGGTTGTATAGTTAAA (SEQ ID NO.: 7) | Pull down Let-7a cDNA |
| UQ-mmu-miR-150 | CCTCTCCCAACCCTTGTACCAGTGAAA (SEQ ID NO.: 8) | Real time PCR forward primer |

TABLE 1-continued

| Name | Sequence | Usage |
|---|---|---|
| UQ-mmu-let-7a | GGTTGGAGTAACACTTGAGGTAGTAGGTTGTATAGTTAAA (SEQ ID NO.: 9) | Real time PCR forward primer |
| UQ-mmu-miR-142-3p | CGTCATAGCATCATTGTAGTGTTTCCTACTTTATGGAAAA (SEQ ID NO.: 10) | Real time PCR forward primer |
| UQ-mmu-miR-1971 | TCCCAGTAAAGGCTGGGCTGAGAAAA (SEQ ID NO.: 11) | Real time PCR forward primer |
| UQ-mmu-miR-10a | CAAGTTAGAAGTACCCTGTAGATCCGAATTTGTGAAA (SEQ ID NO.: 12) | Real time PCR forward primer |
| UQ-mmu-let-7b | CAACTTGTCTGAGGTAGTAGGTTGTGTGGTTAAA (SEQ ID NO.: 13) | Real time PCR forward primer |
| UQ-mmu-let-7e | ACCTTGGGTGAGGTAGGAGGTTGTATAGTTAAA (SEQ ID NO.: 14) | Real time PCR forward primer |
| UQ-mmu-let-7g | GGTGGAGCCTGAGGTAGTAGTTTGTACAGTTAAA (SEQ ID NO.: 15) | Real time PCR forward primer |
| UQ-mmu-miR-669h-5p | CGTCATGCATGGGTGTATAGTTGAGTGCAAA (SEQ ID NO.: 16) | Real time PCR forward primer |
| UQ-mmu-miR-1 | CCTCTTAGTGCACTGGTGGAATGTAAAGAAGTATGTATAAA (SEQ ID NO.: 17) | Real time PCR forward primer |
| UQ-mmu-miR-1961 | GGTCGACTTCCCATTAGATGAGGTAGTAGTTAGAAAAA (SEQ ID NO.: 18) | Real time PCR forward primer |
| UQ-mmu-miR-1-2-as-3p | CATCAGTCCTGGGTACATAAAGAAGTATGTGCAAA (SEQ ID NO.: 19) | Real time PCR forward primer |
| UQ-mmu-miR-206 | CACATTGATTGGAATGTAAGGAAGTGTGTGGAAA (SEQ ID NO.: 20) | Real time PCR forward primer |
| UQ-mmu-miR-100 | GGTTCAACCCGTAGATCCGAACTTGTGAAA (SEQ ID NO.: 21) | Real time PCR forward primer |
| UQ-mmu-miR-99a | CCTCCTAACCCGTAGATCCGATCTTGTGAAA (SEQ ID NO.: 22) | Real time PCR forward primer |
| UQ-mmu-miR-10a | CAAGTTAGAAGTACCCTGTAGATCCGAATTTGTGAAA (SEQ ID NO.: 23) | Real time PCR forward primer |
| UQ-mmu-miR-3082-5p | ACTCGACAGAGTGTGTGTGTCTGTGTAAA (SEQ ID NO.: 24) | Real time PCR forward primer |
| UQ-mmu-miR-466I-5p | GGCGAAGCCTTGTGTGTACATGTACATGTATAAA (SEQ ID NO.: 25) | Real time PCR forward primer |

For Table 1,
V = A, G, or C;
N = A, G, C, or T.

One or more oligo-probes 106 can also be included in the qPCR reaction. In some embodiments, the qPCR reaction can include about 2 to about 50 amplification cycles. In further embodiments, a final extension step can be performed after all the amplification cycles have been performed. In yet further embodiments, the reaction include an initial denaturation step that occurs prior to any of the amplification cycles. In other embodiments, the qPCR protocol includes one or more cycles to determine the Tm of the PCR product (amplicon) produced in each reaction.

In some embodiments, an amplification cycle can be a 3 step-cycle that includes a denaturing step, an annealing step, and an extension step. The denaturing step can be performed at about 95° C. for about 30 seconds to about 2 minutes. The annealing step can be performed at about 50° C. to about 65° C. for 30 seconds to about 2 minutes. The extension step can be performed at about 72° C. for about 30 seconds to about 2 minutes.

In some of these embodiments, in at least one amplification cycle of the qPCR reaction, the oligo-probes 106 can anneal to a template molecule produced during the denaturing step of the qPCR cycle. If both the universal reverse primer and the target-specific forward primer also hybridize to a template molecule, an amplicon can be generated during the extension phase of the qPCR cycle. When the amplicon is generated, the probe molecule on the oligo-probe 106 can be unquenched and generate a signal 107*a*, 107*b*, 107*c*, 107*d*. The signal can be detected by a detector in the qPCR machine that is configured to detect that particular signal. This process can be repeated for each cycle in the qPCR reaction protocol. Insofar as each subject's cDNA can be configured to be hybridized by a different oligo-probe, the signal produced from each subject's cDNA 107*a*, 107*b*, 107*c*, 107*d* (assuming the target sequence is present within the cDNA) can be different from the other signals generated from cDNA isolated from different subjects and prepared with different RT stem-loop adapter primers.

In other embodiments, an amplification cycle can be a 2-step PCR cycle. The number of amplification cycles per qPCR protocol can range from about 2 cycles to about 50 cycles. In some embodiments, the qPCR protocol can begin with an initial denaturation step at about 95° C. for about 1 to about 5 minutes. Each amplification cycle can contain a denaturing step that can be about 10 to about 30 seconds and can be conducted at about 95° C. Each amplification cycle can also include an annealing/extension step that can range from about 30 seconds to about 2 minutes and can be conducted at about 60° C. to about 70° C.

In some of these embodiments, the target-specific forward primers can be configured to include additional sequences at the 5' and 3' ends such that annealing/extension occur in the same step in a PCR cycle. If a miRNA has a Tm value lower than 70° C., the Tm of a forward qPCR primer can be adjusted by adding an extra sequence to the 5' end of the primer. The extra sequence can be an artificial sequence that does not form hairpin structure with the sequence it is attached to, does not have homology with the known mature and pre-miRNA sequences, and does not contain a stretch of more than 4 guanosine nucleotides. If a miRNA has a Tm higher than 70° C., the Tm of a target-specific forward qPCR primer can be adjusted by truncating the 5' end of this miRNA. At the 3' ends of the forward primers, three or more adenosine nucleotides are added. The different mRNA/miRNAs can be distinguished from one another based on differences (e.g. wavelength differences) as previously described.

Figure 2:
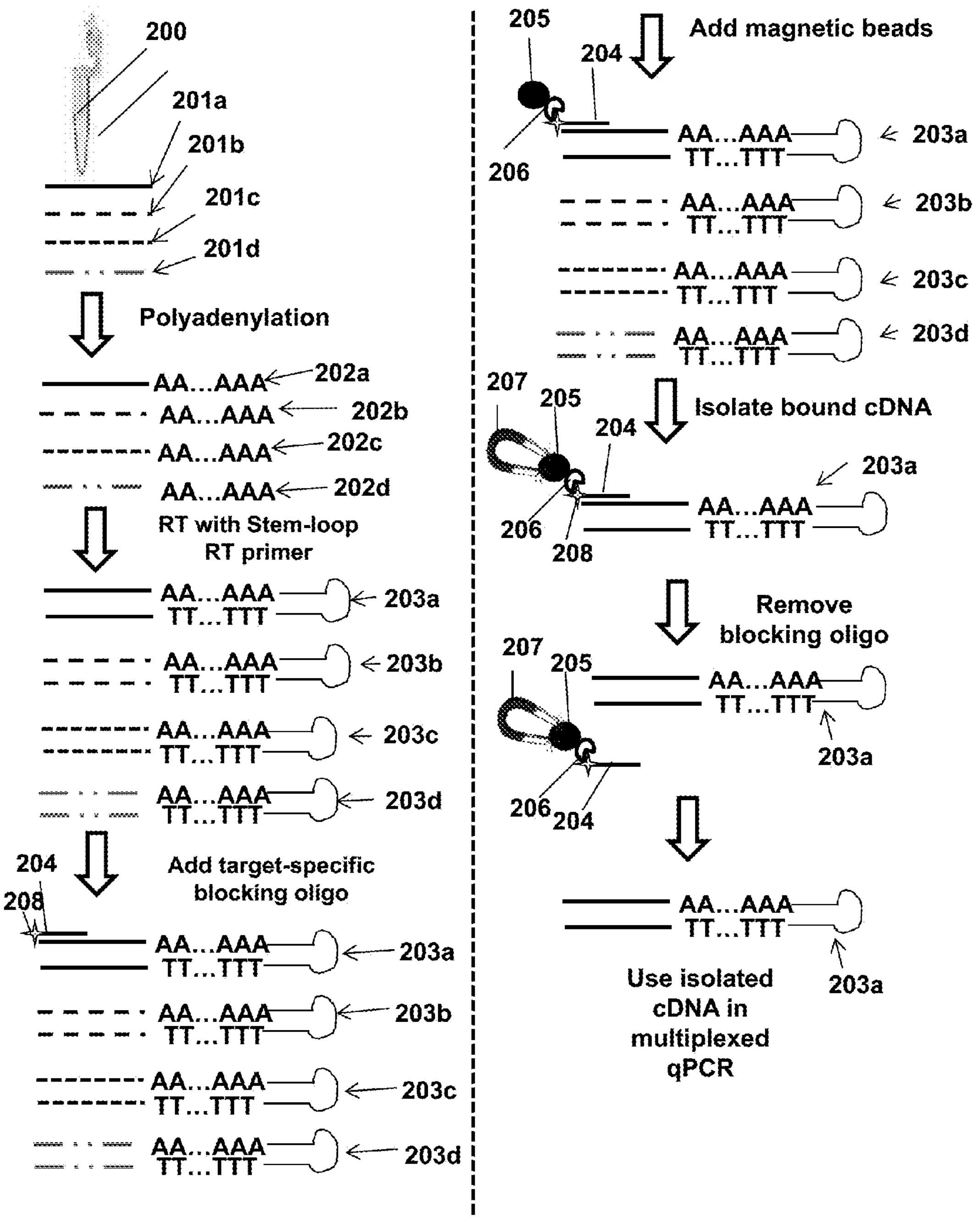
FIG. 2 shows one embodiment of a method for preparing cDNA from miRNA or mRNA for use in the universal multiplexed qPCR assay shown in FIG. 3.

Attention is now directed to FIG. 2, which illustrates another embodiment of a method to simultaneously detect one or more different molecules of miRNA/mRNA in a single reaction. The method can begin by isolating total RNA, which includes mRNA and/or miRNA, from a subject. The isolated total RNA can be separated into aliquots. For example, each aliquot can be placed in separate tubes. In some embodiments, one aliquot containing multiple different RNA molecules (including miRNA and/or mRNA) 201*a*, 201*b*, 201*c*, 201*d* (collectively 201) can be placed in tube or other container 200. While only 4 different RNA molecules are shown in FIG. 2, it will be appreciated that this number can be greater than 4. In the embodiment shown in FIG. 2, each RNA molecule 201 corresponds to a different miRNA or mRNA. The RNA molecules 201 can then be polyadenylated as described with respect to FIG. 1. This forms polyadenylated RNA molecules 202*a*, 202*b*, 202*c*, and 202*d* (collectively 202).

The polyadenylated RNA molecules 202 can be used as templates for reverse transcription (RT) with a Stem-loop primer adapter 203*a*, 203*b*, 203*c*, 203*d* (collectively 203) as described in relation to FIG. 1. In FIG. 2, the Stem-loop primer adapters 203*a*-203*d* contain the same oligo-probe hybridization sequence. Thus, all 4 different RNA molecules prepared in this sample will be detected by the same probe and generate the same type of signal, if an amplicon is produced from them during subsequent qPCR. RT can result in cDNA molecule(s), which incorporate the stem-loop stem primer adapter.

Figure 3:
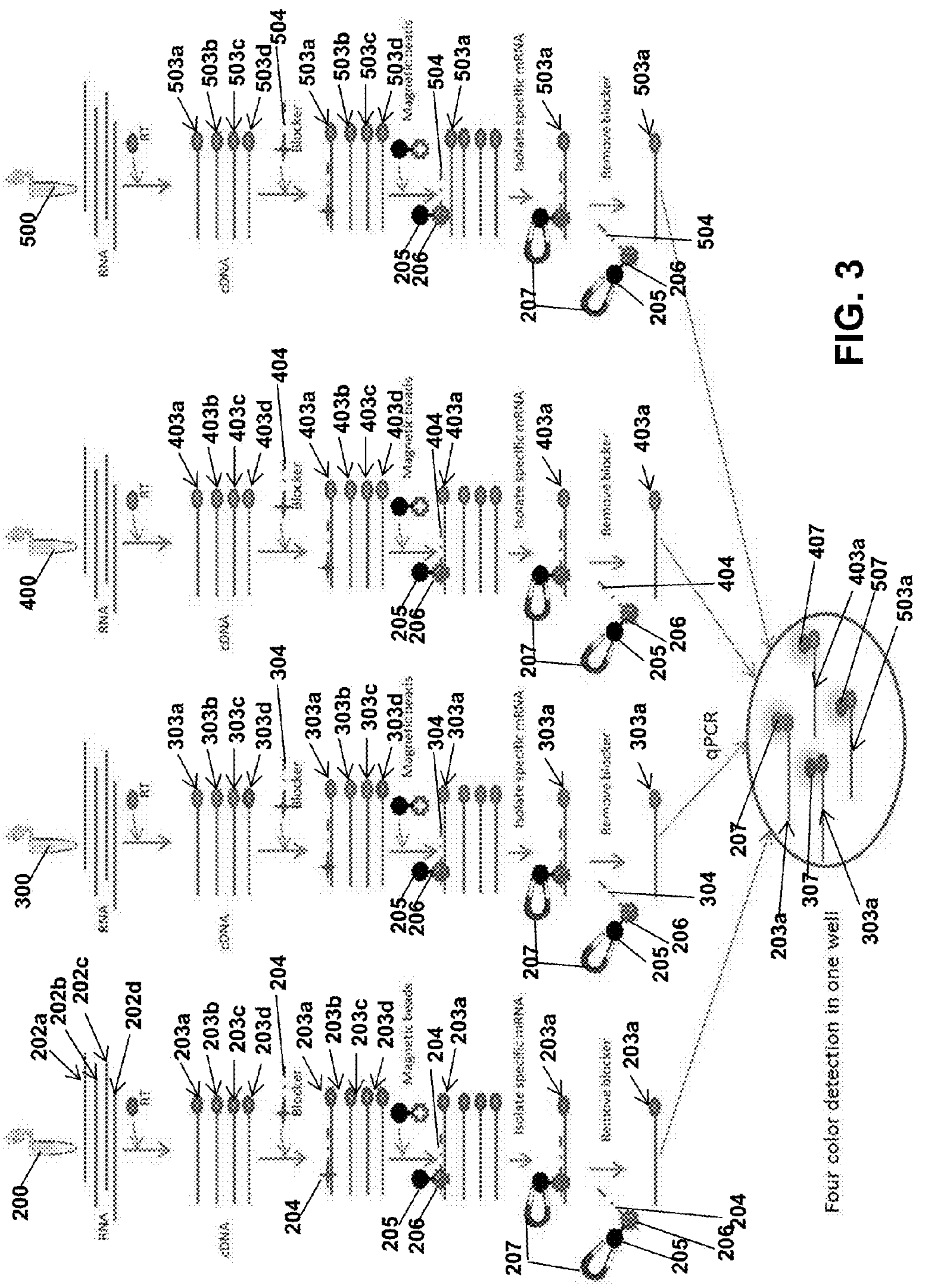
FIG. 3 shows another embodiment of a universal multiplexed qPCR assay for detecting RNA molecules, particularly miRNA and mRNA, in a sample that utilizes a pull-down assay.

Next, a target-specific blocking oligo 204 can be added to the cDNA molecules previously generated. The target-specific oligo 204 can hybridize with a cDNA molecule having a complementary sequence (e.g. 203*a*). Thus, the target-specific oligo 204 can specifically hybridize with cDNA molecule(s) corresponding target sequence of interest (e.g. 203*a*). The target-specific oligo 204 can be bound to a molecular tag 208, which can allow substrate specific isolation of the bound target cDNA molecule. Suitable molecular tags include, but are not limited to, biotin, peptides (e.g. FLAG sequence, HQ sequence, and poly-histidine sequences), proteins (e.g. glutathione S-transferase, fluorescent proteins, and c-Myc). The molecular tag 208 allows for direct or indirect affinity purification by methods generally known. In one embodiment, and as shown in FIG. 3, the molecular tag 208 is biotin.

Following specific hybridization of the target-specific oligo 204 to the target sequence in the cDNA molecule, the bound cDNA molecule(s) can be separated from un-bound cDNA molecule(s). In some embodiments, the cDNA molecules (bound and un-bound to a target specific oligo 204) can be incubated with magnetic beads 205. The magnetic beads 205 can be bound to a molecular substrate 206 that can specifically bind the molecular tag 208. In some of these embodiments the molecular substrate 206 can be strepavidin. In other embodiments, the molecular substrate can be an antibody, aptamer, or a metal (e.g. copper or nickel). The bound cDNA molecules can be separated by exposing the reaction contents containing the bound and unbound cDNA to a magnetic field 207.

In other embodiments, magnetic beads 205 are not used and the bound cDNA molecule(s) can be separated directly via the molecular substrate 206. In other words, just a molecular substrate 206 can be used to bind the molecular tag 208. In a subsequent step, a pull down assay or other similar technique can be performed that is specific for the molecular tag 208. For example, a molecular tag specific antibody can be used to specifically bind the molecular tag

208. In some of these embodiments, the bound cDNA molecule can be separated by an immunoglobulin pull-down assay, which can directly isolate the bound cDNA molecules that are specifically bound by an antibody or fragment thereof.

After isolation of the bound cDNA, which can contain the target sequence, the bound cDNA can be used as the template in a multiplexed qPCR reaction with other bound cDNA molecules that contain different target sequences and different RT stem-loop primer adapters that are specific for different oligo-probes. With this in mind, attention is directed to FIG. 3, which demonstrates other embodiments of a multiplexed miRNA/mRNA qPCR assay. As shown in FIG. 3, the steps shown in FIG. 2 are repeated for each desired target sequence (e.g. a gene sequence). As such, in this example a sample of isolated RNA from a subject are divided into 4 aliquots 200, 300, 400 and 500. In parallel, the steps outlined in FIG. 2 are performed. However, each different aliquot 200, 300, 400, and 500 are exposed to different target-specific oligos 204, 304, 404, and 504 and different RT stem-loop primer adapters 203*a-d* (203), 303*a-d* (303), 403*a-d* (403), and 503*a-d* (503) are used.

As described in relation to FIG. 1, the RT stem-loop primer adapters 203, 303, 403, and 503 each contain a different oligo-probe hybridization sequence. In this way, all molecules with RT stem-loop primer adapter 203 can be detected by a signal (assuming an amplicon is generated from the cDNA molecule 203*a* during qPCR) that is different from the signal that is generated from cDNA molecule 303*a*, 403*a*, 503*a* with RT stem-loop primer adapter 303, 403 or 503, respectively. Again, this assumes an amplicon is produced during qPCR to cause unquenching of the molecular probe molecule. Similarly, the other cDNA molecules 303, 403, and 503 can produce different signals depending on the RT stem-loop primer adapter used, thus allowing for multiplexing.

Following parallel performance of the steps as illustrated in FIG. 2, the separated bound cDNA molecules 203*a*, 303*a*, 403*a*, and 503*a* can be used as templates in a qPCR protocol as previously described. The separated bound cDNA molecules 203*a*, 303*a*, 403*a*, and 503*a* can be analyzed in a single qPCR reaction as illustrated in FIG. 4. As described in FIG. 2, oligo-probes 207, 307, 407, and 507 can be unquenched when an amplicon is produced from a given cDNA template 203*a*, 303*a*, 403*a*, or 503*a* and can generate signal(s) that are distinguishable from one another (e.g. each signal can produce or can be a different wavelength of light). As such, by combining a different target-specific oligos 204, 304, 404, and 504 each with a different RT stem-loop primer adapter 203, 303, 403, or 503, the products resulting from the pull-down or affinity isolation of the bound cDNA molecule(s) 203*a*, 303*a*, 403*a*, and 503*a* can be assayed and distinguished from one another simultaneously for target sequence expression the same qPCR reaction. Although only four different reactions are multiplexed in the embodiments illustrated in FIGS. 1 and 3, the number of reactions that can be multiplexed only limited as to what the assay can allow for. As shown in FIG. 4, the various embodiments of the assay described herein can allow for at least 1536 different samples or different miRNA/mRNA to be analyzed in a single 384 well plate.

Materials and Reagents

Materials for detecting, quantifying and/or profiling mRNA and/or miRNA are also provided herein. The materials can include: at least one RT stem-loop primer adapter for reverse transcription of mRNA and/or miRNA and hybridizing to an oligo-probe, a universal reverse primer for PCR amplification that can hybridize with a sequence within the RT stem-loop primer adapter, and an oligo probe that can be specific for the RT stem-loop primer adapter. The materials can also include a target-specific forward primer for PCR amplification. The materials can also include a molecular substrate. In some embodiments, the molecular substrate can be bound to a magnetic bead. The materials can also include a target-specific oligo bound to a molecular tag. The primers and other nucleotides can be provided as salts thereof and can be in liquid or lyophilized form.

The RT stem-loop primer adapter can contain an oligo dT region that can hybridize with a poly A region of polyadenylated mRNA and miRNA molecules. The RT stem-loop primer adapter also can contain an oligo-probe hybridization sequence that can specifically hybridize with an oligo-probe. Exemplary sequences for the RT stem-loop primer adapter can be found in FIGS. 12 and 13. The hybridization sequence in RT stem-loop primer adapter can be modified so as to hybridize with different oligo-probes as described elsewhere herein.

The oligo-probe can contain an oligonucleotide that is bound to a quenched molecular probe. In some embodiments, the molecular probe can be made of a fluorescent molecule and a quencher. In some of these embodiments, the quencher can be bound at one end of the oligonucleotide and the fluorescent molecule is bound to the other end. When the oligo-probe is not bound to a template cDNA molecule, the quencher can interact with the fluorescent molecule so as to quench light emission from the fluorescent molecule. In some embodiments, quenching can occur by the quencher, where the quencher can induce a conformational change in the fluorescent molecule upon interaction with the fluorescent molecule. When the oligo-probe is hybridized, hybridization can interrupt the interaction between the quencher and the fluorescent molecule such that light can be emitted from the fluorescent molecule. Suitable fluorescent molecules have been previously described in relation to the molecular probe of FIG. 1.

One issue plaguing current attempts at multiplexing qPCR assays is addressing the need for homogenous amplification of the targets nucleotides (including miRNAs or mRNAs). In the human genome, the predicted miRNA Tm values range from 48 to 86° C. with a mean of 66° C., and the calculated miRNA GC percentages range from 9 to 95% with a mean of 51%. Tm value and GC content are the two most important parameters in PCR amplification that have great effects on amplification efficiency. With such broad ranges of Tm value and GC content, if using the miRNA sequences as the forward primers because the sizes of miRNAs are the same as that of a regular primer, one would expect that it is impossible to homogeneously amply all miRNAs under the same condition, which is desirable for high throughput miRNA profiling.

Using same amount of starting miRNA templates, RT-qPCR results obtained using traditional techniques demonstrate that the relative levels of miRNAs can be over 200 times different due to different amplification efficiency. The Tm and GC content variation problem in miRNA detection can be addressed in order to achieve homogeneous amplification. To overcome these issues, the embodiments described herein can contain miRNA (or mRNA) specific primers as the forward primers that are designed such that the Tm variation of all the primers can be within ±1° C. of one another by adding extra sequences at the 5' end of those miRNAs that have lower Tm or by truncating the 5' end of those miRNAs that have higher Tm values. Thus, all designed primers can have predicted Tm values of 70±1° C.

The additional sequences can be artificial sequences that do not form hairpin structures with the sequence they are attached to, can have homology with the known mature and pre-miRNA sequences, and can contain a stretch of more than 4 guanosine nucleotides.

Kits

The materials, as previously described, can be provided in kits for detecting, quantifying and/or profiling mRNA and/or miRNA. In one embodiment, the kit can include at least one RT stem-loop primer adapter for reverse transcription of mRNA and/or miRNA and hybridizing to an oligo-probe. The kit can further include a universal reverse primer for PCR amplification that hybridizes with a sequence within the RT stem-loop primer adapter. The kit can also include target-specific forward primer for PCR amplification, molecular substrate that is bound or not bound to a magnetic bead, and/or a target-specific oligo bound to a molecular tag. The kits can also include microwell plates that contain an array of wells configured for use in a thermocycler, such as a real-time PCR machine. The kits can also include other container(s) for performing the reaction in. One or more of the materials previously described can pre-distributed within the wells of a plate provided in a kit.

The kits may also include reagents for isolating miRNA or RNA and/or polyadenalyting the miRNA or performing any step of the assay. Optionally, the kit may include any material useful for performing any step of the assay described herein. For instance, the kit may further contain any material useful for reverse transcription of RNAs, and/or for profiling the target RNA. For instance, the kit may poly(A)polymerases, dNTPs, Adenosine-5'-triphosphates (ATP), DNA ligases (e.g., T4 DNA ligase), and Taq DNA polymerase.

The kit may also optionally contain e. g., a buffering agent, a preservative, or a stabilizing agent. Each component of the kit is usually enclosed within an individual container and all of the various containers are within a single package along with instructions contained in a tangible medium of expression (e. g., printed instructions).

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Multiplexed qPCR Assay for miRNA

Materials and Methods

Materials and Reagents:

Pierce Streptavidin Magnetic Beads

Magnetic stand

Binding/Wash buffer (25 mM Tris, 0.15 M NaCl, 0.1% Tween-20 detergent, $H_2O$)

Wash buffer (20 mM Tris-HCl pH 7.5, 500 mM LiCl, 1 mM EDTA)

Low-Salt Wash Buffer (20 mM Tris-HCl pH 7.5, 200 mM LiCl, 1 mM EDTA)

Elution Buffer (20 mM tris-HCl pH 7.5, 1 mM EDTA)

Premix Ex Taq™

SYBR Premix II Ex Taq™

Nucleotide primers: See FIGS. 11 and 12 for sequences.

A mutliplexing qPCR assay was performed following the methods illustrated in FIG. 1. Here, only 2 different RT stem-loop adapter primers were used. One contained a sequence that hybridizes with an oligo-probe bound to FAM. The other RT stem-loop adapter primer contained a sequence that hybridizes with an oligo-probe bound to VIC. Total RNA from pooled ten pathogenic samples was prepared in accordance with the steps illustrated and described in relation to FIG. 1. The RNA was separated into two aliquots (one for use with the FAM oligo-probe and one for use with the VIC oligo probe) and the RT and other preparation methods as illustrated and described in FIG. 1 were performed in parallel on the two aliquots of the RNA sample. This resulted in cDNA templates that would be hybridized by either the FAM oligo-probe or the VIC oligo-probe. qPCR was then performed on using the cDNA as templates. Each qPCR reaction contained both cDNA templates.

In one assay, the cDNA templates were used to detect a set of 96 miRNAs. As such, the ability of each RT stem-loop primer adapter/oligo-probe pair to detect the same set of 96 different miRNAs was evaluated. In a second assay, 8 different mRNA sequences were evaluated in the same cDNA samples.

Results

Figure 5A:
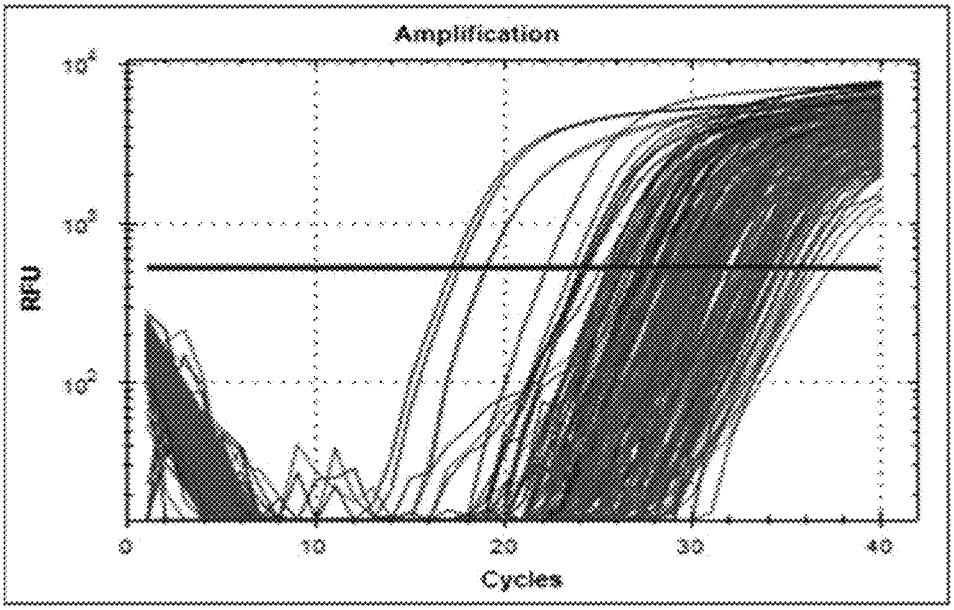
FIGS. 5A and 5B show the real-time PCR amplification curves of a multiplexed assay for analyzing 96 miRNAs (FIG. 5A) or 8 mRNAs (FIG. 5B).
Figure 5B:
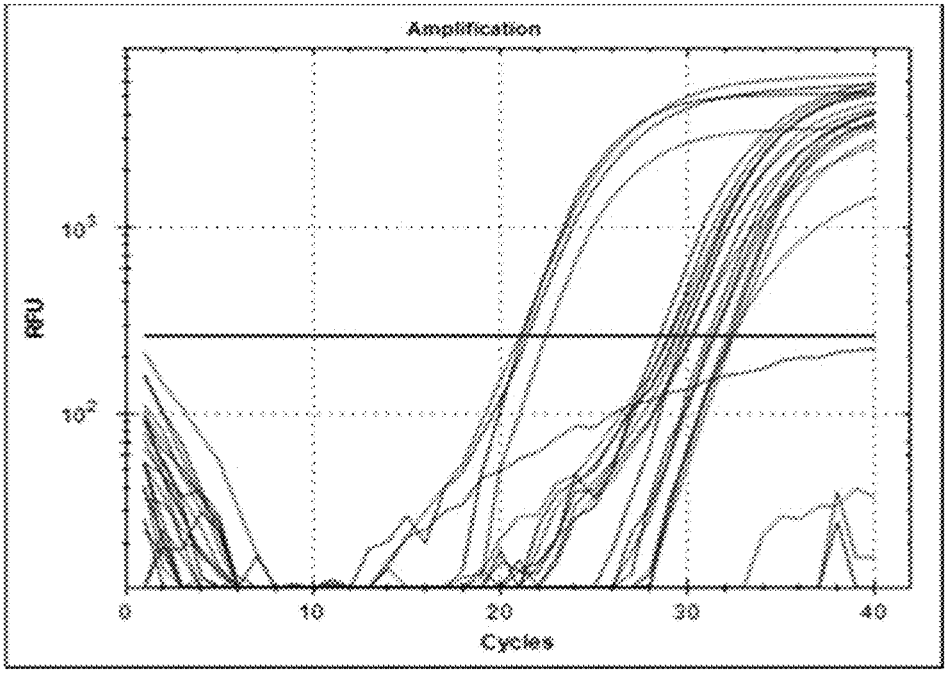

The real-time PCR amplification curves of the multiplexed assay for analyzing the 96 miRNAs is shown in FIG. 5A. The real-time PCR amplification curves of the multiplexed assay for analyzing the 8 mRNAs are shown in FIG. 5B.

Example 2: Multiplexed Pull-Down qPCR Assay for miRNA

Introduction

To confirm the results obtained in Example 1, individual target-specific pull down assays as described in FIGS. 2 and 3, on the cDNA prepared in Example 2 was performed.

Multiplexed qPCR Assay

Figure 6A:
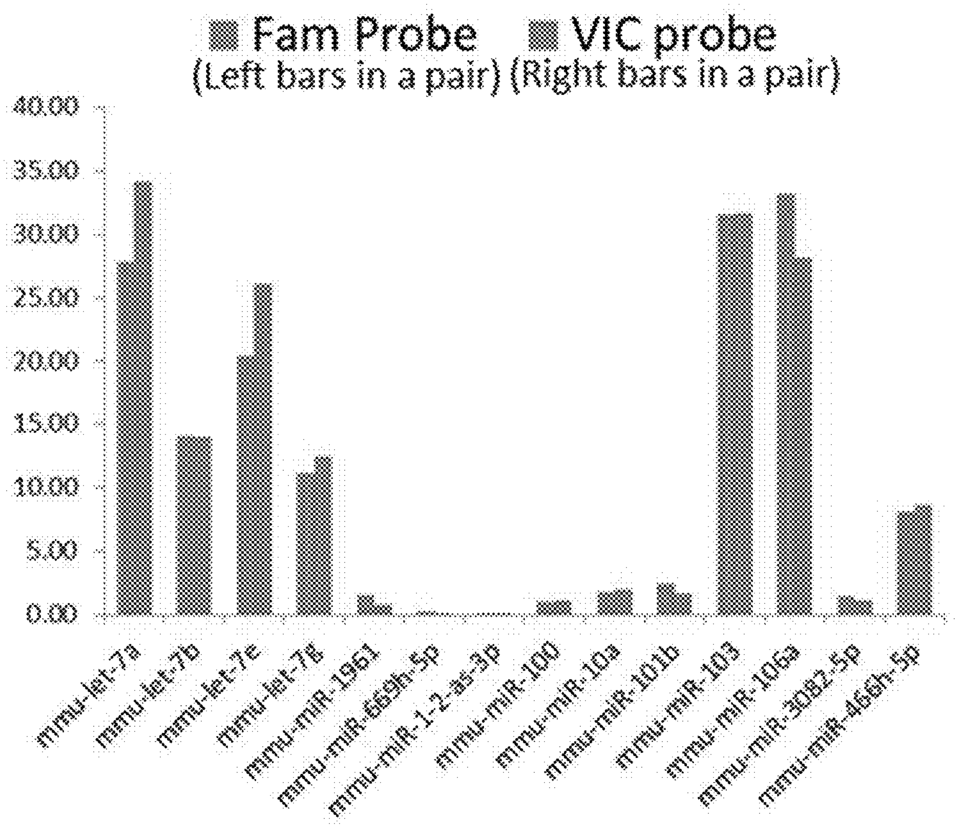
FIGS. 6A and 6B show the results from individual real-time PCR performed on a subset of the 96 miRNAs analyzed in FIGS. 5A and 5B (FIG. 6A).

Biotinized target-specific oligos were prepared by adding biotins to the 3'-ends of oligos by using 10 units of Terminal Deoxynucleotidyl Transferase (TdT), Oligo (1 μM) and Biotin-11-UTP (5 μM) in a 50 μl of volume, 37° C. for 30 minutes. Biotinized target-specific oligos also were synthesized by adding Biotin to the 5'-ends of oligos using either a C6 spacer arm (IDTDNA, Coralville, Iowa, USA). The miRNA targets analyzed are shown in FIG. 6A. The biotinized target-specific oligos were diluted to about 100 nM and about 6 μl of it was combined with about 6 μl of the cDNA sample from RT-PCR. Pierce streptavidin magnetic beads were washed by adding 50 μl of beads to 200 μl of Binding/Wash buffer in a 1.5 mL tube, mixing for about 2 minutes by pipetting up and down, and then vortexing briefly. The beads were kept in the buffer until they were to be used.

About 40 μl of Binding/Wash buffer was mixed with the combined samples and then incubated at about 80° C. for about 5 minutes using a PCR machine (Bio-Rad T100 Thermal Cycler). The PCR machine was then turned off for about 30 minutes, allowing the sample to cool to room temperature. At this point, about 1 μl of the sample was analyzed spectrophotometrically using a Nanodrop spectrophotometer to determine the concentration of the cDNA.

The previously washed magnetic beads were removed from the supernatant by using the magnetic stand. The supernatant was discarded. The sample was added to the washed beads with about 40 μl of Binding/Wash buffer and then incubated for about 30 minutes at room temperature with agitation. After incubation, the supernatant was separated from the beads using the magnetic stand and transferred to a fresh 1.5 mL tube.

After the supernatant was removed, about 250 μl of Binding/Wash buffer was added to the beads and then incubated at about 50° C. in a water bath for about 5 minutes. The sample was removed from the water bath and then mixed with agitation by pipetting up and down. The supernatant was separated from the beads by using the magnetic rack and then discarded.

After the supernatant was discarded, about 250 μl of Wash buffer was added to the beads and then incubated at about 50° C. in a water bath for about 5 minutes. The sample was removed from the water bath and then mixed with agitation by pipetting up and down. The supernatant was separated from the beads by using the magnetic rack and then discarded. This process was repeated once.

After repeating the above, about 250 μl of Low-Salt Wash Buffer was added to the beads. It was incubated at about 50° C. in a water bath for about 5 minutes. The sample was removed from the water bath and then mixed with agitation by pipetting up and down. The supernatant was separated from the beads by using the magnetic rack and then discarded.

To elute the sample from the beads, about 50 μl of elution buffer was added after the supernatant was discarded. The beads are vortexed gently to suspend them and then incubated at about 80° C. in a water bath for about 5 minutes with occasional agitation. The supernatant was separated from the beads using the magnetic stand and transferred to a fresh 1.5 mL tube. The supernatant was then analyzed spectrophotometrically using a Nanodrop spectrophotometer to determine concentration. This sample was then used as a template for the real-time qPCR. Real-time qPCR was then performed to verify the specific pull-down of miRNA. The qPCR protocol used was as follows:

Initial denaturation: 95° C. 2 minutes

PCR: 40 cycles of 95° C. 15 seconds followed by 65° C. 1 minute

Figure 6B:
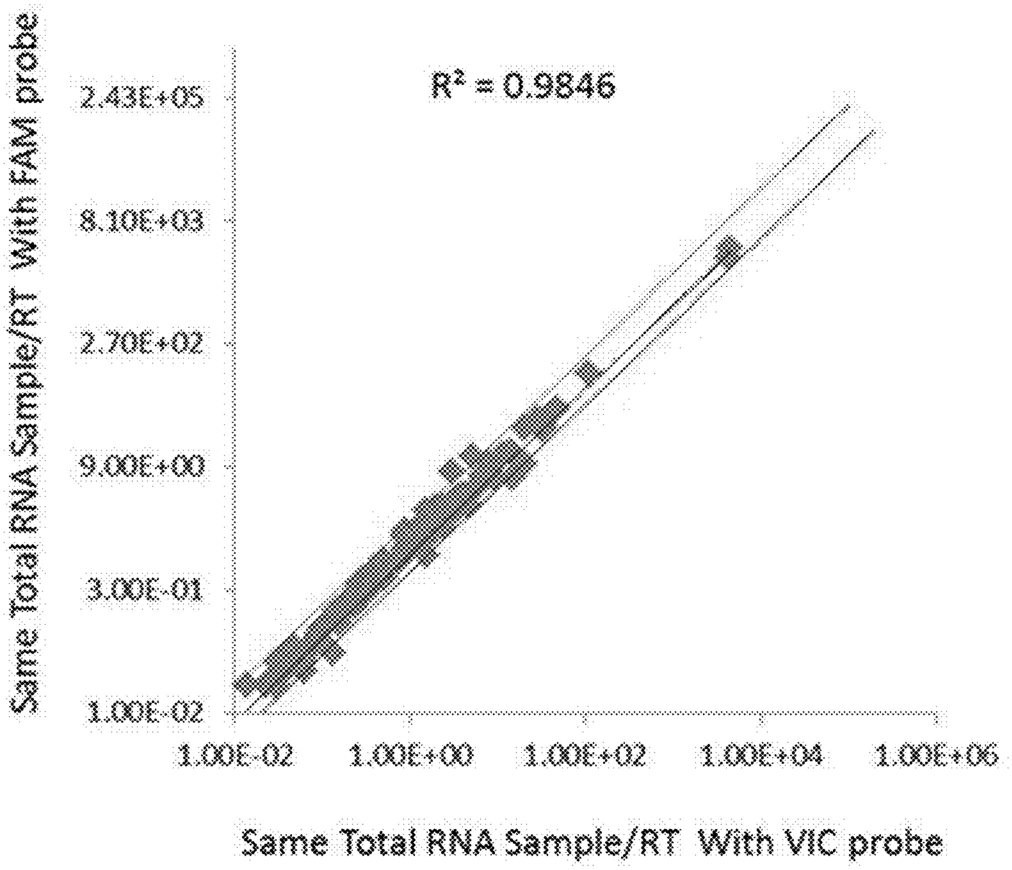

Results:

As demonstrated in FIGS. 6A and 6B, the multiplexed assay performed in Example 1 agrees with the results shown in FIGS. 6A and 6B. As demonstrated in FIG. 6B, the results obtained from the PCR reactions performed with the FAM oligo-probe were highly correlated ($R^2$=0.9846) with the results obtained from the PCR reactions performed with the VIC oligo-probe. Table 2 shows the numerical data of a duplexed RNA qPCR assay of 96 miRNAs. These data demonstrate that the assay is not dependent on TAM or VIC, but rather is dependent on the amount of RNA in the samples. In other words, the same results will be obtained using TAM or VIC probes for the same miRNAs in the same samples.

TABLE 2

| | Quantification cycle (Cq) | | Normalized expression levels | | Ratio |
|---|---|---|---|---|---|
| MicroRNAs | FAM | VIC | FAM | VIC | FAM/VIC |
| mmu-let-7a | 26.3 | 24.4 | 27.9 | 34.2 | 1 |
| mmu-let-7b | 27.3 | 25.7 | 14.1 | 14.0 | 1 |

TABLE 2-continued

| | Quantification cycle (Cq) | | Normalized expression levels | | Ratio |
|---|---|---|---|---|---|
| MicroRNAs | FAM | VIC | FAM | VIC | FAM/VIC |
| mmu-let-7e | 26.7 | 24.8 | 20.4 | 26.1 | 1 |
| mmu-let-7g | 27.6 | 25.8 | 11.2 | 12.4 | 1 |
| mmu-miR-1961 | 30.5 | 29.8 | 1.5 | 0.8 | 2 |
| mmu-miR-669h-5p | 33.2 | 31.8 | 0.2 | 0.2 | 1 |
| mmu-miR-1-2-as-3p | 34.0 | 33.7 | 0.1 | 0.1 | 2 |
| mmu-miR-100 | 31.1 | 29.3 | 1.0 | 1.1 | 1 |
| mmu-miR-10a | 30.2 | 28.5 | 1.8 | 2.0 | 1 |
| mmu-miR-101b | 29.8 | 28.7 | 2.4 | 1.7 | 1 |
| mmu-miR-103 | 26.1 | 24.5 | 31.6 | 31.7 | 1 |
| mmu-miR-106a | 26.0 | 24.6 | 33.2 | 28.2 | 1 |
| mmu-miR-3082-5p | 30.5 | 29.3 | 1.5 | 1.2 | 1 |
| mmu-miR-466h-5p | 28.1 | 26.3 | 8.1 | 8.7 | 1 |
| mmu-miR-466f-5p | 33.8 | 32.1 | 0.2 | 0.2 | 1 |
| mmu-miR-669d | 36.2 | 35.0 | 0.0 | 0.0 | 1 |
| mmu-miR-669o-5p | 33.3 | 31.5 | 0.2 | 0.2 | 1 |
| mmu-miR-466d-5p | 35.7 | 34.4 | 0.0 | 0.0 | 1 |
| mmu-miR-669a-5p | 33.0 | 30.9 | 0.3 | 0.4 | 1 |
| mmu-miR-3097-5p | 29.8 | 28.5 | 2.4 | 2.0 | 1 |
| mmu-miR-670 | 26.7 | 26.2 | 20.4 | 9.5 | 2 |
| mmu-miR-294 | 32.6 | 31.1 | 0.3 | 0.3 | 1 |
| mmu-miR-468 | 31.3 | 29.0 | 0.9 | 1.3 | 1 |
| mmu-miR-495 | 34.1 | 32.5 | 0.1 | 0.1 | 1 |
| mmu-miR-133b | 30.2 | 28.5 | 1.9 | 1.9 | 1 |
| mmu-miR-380-5p | 32.1 | 30.7 | 0.5 | 0.4 | 1 |
| mmu-miR-135b | 35.6 | 34.2 | 0.0 | 0.0 | 1 |
| mmu-miR-200a | 34.5 | 32.9 | 0.1 | 0.1 | 1 |
| mmu-miR-146a | 28.5 | 27.0 | 6.1 | 5.4 | 1 |
| mmu-miR-148a | 28.1 | 26.1 | 7.9 | 10.0 | 1 |
| mmu-miR-152 | 32.2 | 30.4 | 0.5 | 0.5 | 1 |
| mmu-miR-28 | 29.9 | 27.9 | 2.3 | 3.0 | 1 |
| mmu-miR-3093-5p/10 | 33.3 | 31.6 | 0.2 | 0.2 | 1 |
| mmu-miR-15b | 24.3 | 22.5 | 110.0 | 120.7 | 1 |
| mmu-miR-195 | 30.4 | 28.7 | 1.6 | 1.7 | 1 |
| mmu-miR-181c | 29.1 | 27.4 | 4.0 | 4.1 | 1 |
| mmu-miR-193 | 33.7 | 32.1 | 0.2 | 0.2 | 1 |
| mmu-miR-1931 | 30.6 | 28.7 | 1.4 | 1.7 | 1 |
| mmu-miR-1935 | 32.7 | 31.0 | 0.3 | 0.3 | 1 |
| mmu-miR-485 | 35.5 | 33.4 | 0.0 | 0.1 | 1 |
| mmu-miR-1937a/100 | 19.0 | 17.5 | 4487.1 | 3916.7 | 1 |
| mmu-miR-1937c/100 | 19.0 | 17.9 | 4304.3 | 2927.4 | 1 |
| mmu-miR-1946b | 33.1 | 31.4 | 0.2 | 0.3 | 1 |
| mmu-miR-743b-5p | 29.2 | 27.5 | 3.6 | 4.0 | 1 |
| mmu-miR-3067 | 32.4 | 30.4 | 0.4 | 0.5 | 1 |
| mmu-miR-882 | 33.0 | 31.1 | 0.3 | 0.3 | 1 |
| mmu-miR-196a | 32.8 | 31.3 | 0.3 | 0.3 | 1 |
| mmu-miR-1971 | 29.6 | 28.1 | 2.7 | 2.5 | 1 |
| mmu-miR-423-3p | 28.4 | 26.7 | 6.6 | 6.9 | 1 |
| mmu-miR-26b | 30.9 | 29.2 | 1.1 | 1.2 | 1 |
| mmu-miR-27b | 31.6 | 30.0 | 0.7 | 0.7 | 1 |
| mmu-miR-292-3p | 35.8 | 33.7 | 0.0 | 0.1 | 1 |
| mmu-miR-292-5p | 32.3 | 30.6 | 0.4 | 0.5 | 1 |
| mmu-miR-302d | 32.9 | 31.5 | 0.3 | 0.2 | 1 |
| mmu-miR-302c | 35.1 | 34.4 | 0.1 | 0.0 | 2 |
| mmu-miR-291a-5p | 32.7 | 30.7 | 0.3 | 0.4 | 1 |
| mmu-miR-29a | 25.6 | 24.0 | 46.3 | 44.5 | 1 |
| mmu-miR-29b | 28.9 | 27.5 | 4.4 | 3.9 | 1 |
| mmu-miR-3070b-3p | 28.8 | 27.8 | 4.7 | 3.1 | 2 |
| mmu-miR-3074-2-3p | 30.0 | 28.5 | 2.1 | 2.0 | 1 |
| mmu-miR-344b | 34.4 | 32.7 | 0.1 | 0.1 | 1 |
| mmu-miR-344c | 27.2 | 26.8 | 14.4 | 6.5 | 2 |
| mmu-miR-344g-3p | 30.1 | 27.9 | 1.9 | 2.9 | 1 |
| mmu-miR-3470b | 30.5 | 28.0 | 1.5 | 2.7 | 1 |
| mmu-miR-434-5p | 28.7 | 25.9 | 5.2 | 12.0 | 0.4 |
| mmu-miR-449a | 34.4 | 33.3 | 0.1 | 0.1 | 1 |
| mmu-miR-34b-5p | 32.8 | 30.7 | 0.3 | 0.4 | 1 |
| mmu-miR-374 | 33.4 | 31.9 | 0.2 | 0.2 | 1 |
| mmu-miR-376b | 36.1 | 34.5 | 0.0 | 0.0 | 1 |
| mmu-miR-412-3p | 31.2 | 28.8 | 0.9 | 1.5 | 1 |
| mmu-miR-455 | 32.1 | 30.0 | 0.5 | 0.7 | 1 |
| mmu-miR-669i | 26.1 | 24.8 | 31.8 | 24.5 | 1 |
| mmu-miR-568 | 37.2 | 35.0 | 0.0 | 0.0 | 1 |
| mmu-miR-489 | 31.2 | 29.7 | 0.9 | 0.9 | 1 |
| mmu-miR-500 | 29.5 | 26.5 | 3.0 | 7.9 | 0.4 |

TABLE 2-continued

| MicroRNAs | Quantification cycle (Cq) FAM | VIC | Normalized expression levels FAM | VIC | Ratio FAM/VIC |
|---|---|---|---|---|---|
| mmu-miR-883a-3p | 35.1 | 34.0 | 0.1 | 0.0 | 1 |
| mmu-miR-105 | 35.1 | 33.8 | 0.1 | 0.0 | 1 |
| mmu-miR-1190 | 35.0 | 33.7 | 0.1 | 0.1 | 1 |
| mmu-miR-1193-3p | 33.8 | 32.5 | 0.2 | 0.1 | 1 |
| mmu-miR-1194 | 34.7 | 33.3 | 0.1 | 0.1 | 1 |
| mmu-miR-1197 | 36.5 | 35.0 | 0.0 | 0.0 | 1 |
| mmu-miR-1199 | 29.5 | 27.7 | 3.1 | 3.5 | 1 |
| mmu-miR-124 | 31.3 | 29.6 | 0.9 | 0.9 | 1 |
| mmu-miR-1249 | 29.5 | 27.8 | 3.0 | 3.1 | 1 |
| mmu-miR-153 | 33.9 | 32.1 | 0.1 | 0.2 | 1 |
| mmu-miR-155 | 29.0 | 27.4 | 4.1 | 4.1 | 1 |
| mmu-miR-182 | 36.1 | 34.1 | 0.0 | 0.0 | 1 |
| mmu-miR-1839-5p | 31.5 | 29.9 | 0.8 | 0.7 | 1 |
| mmu-miR-1843-3p | 30.4 | 29.0 | 1.7 | 1.3 | 1 |
| mmu-miR-185 | 30.7 | 28.7 | 1.3 | 1.7 | 1 |
| mmu-miR-187 | 31.4 | 29.9 | 0.8 | 0.8 | 1 |
| mmu-miR-188-5p | 27.9 | 26.7 | 9.2 | 6.6 | 1 |
| mmu-miR-1895 | 30.3 | 28.4 | 1.7 | 2.1 | 1 |
| mmu-miR-1897-3p | 33.1 | 31.2 | 0.3 | 0.3 | 1 |
| mmu-miR-1898 | 29.4 | 27.7 | 3.2 | 3.4 | 1 |
| mmu-miR-1901 | 29.3 | 27.9 | 3.5 | 2.9 | 1 |

Example 3: Evaluation of miRNA in Aspirin Exacerbated Respiratory Disease (AERD) Via Multiplexed Real-Time qPCR Assay Materials and Methods Total RNA was obtained from the inferior nasal turbinates of 30 subjects (10 with nasal polyps and AERD; 10 with nasal polyps and without AERD; and 10 healthy controls). All qPCR reactions were carried out using Premix Ex Taq™ or SYBR Premix II Ex Taq (Clontech Laboratories, Mountain View, Calif., USA). Total RNA from the samples was prepared similarly to the total RNA in Example 1. Briefly, Total RNAs were extracted from nasal cells collected from 10 subjects with nasal polyps and AERD and pooled (AERD group), as well as from 10 subjects with nasal polyps and without AERD and pooled (nasal polyps and without AERD group). The miRNAs from the two pooled RNA samples were polyadenylated and then reversely transcribed with two universal RT primers with different probe binding sites. Equal amount of cDNAs were mixed together and detected by qPCR with a FAM probe and a VIC probe for each miRNA in the same PCR well with a 96 well plate format. The two levels of each miRNAs from the two samples were compared.

Additionally, the miRNAs with different levels in the two groups were chosen and the levels of each miRNA were measured in the 10 total RNA samples separately.

To determine the specificity of the multiplexed assay, 2 mixtures containing the same amounts of three synthetic miRNAs, miR-142, miR-150 and Let-7a, were polyadenylated and reverse transcribed using RT stem-loop primer adapters. The miR-150 and Let-7a cDNAs were and pulled down by biotinized miR-150 or Let-7a primers with streptavidin magnetic beads and detected by real time PCR. The samples exposed to the miR-150 specific biotinized oligo contained cDNA made with a RT stem-loop primer that would bind a VIC oligo-probe. The specific combinations are shown in FIG. 10.

The samples exposed to the Let-7a-specific biotinized oligo contained cDNA made with a RT stem-loop primer that would bind a FAM oligo-probe. The bound cDNAs were separated by incubating the bound cDNAs with magnetic beads bound to strepavidin and then subsequently exposing them to a magnetic field. Unbound molecules were washed away. The levels of the miRNAs in the pull-down products were detected with real time PCR using VIC and FAM oligo probes and a target-specific forward primer and a universal reverse primer.

Results

Figure 7A:
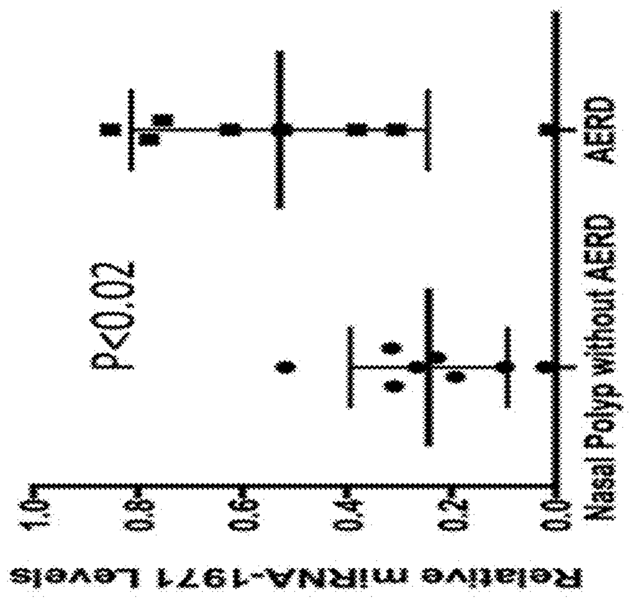
FIGS. 7A and 7B show the expression levels of miRNA-1971 (FIG. 7A) and miRNA-10 a (FIG. 7B) as determined by a multiplexed real-time PCR assay.
Figure 7B:
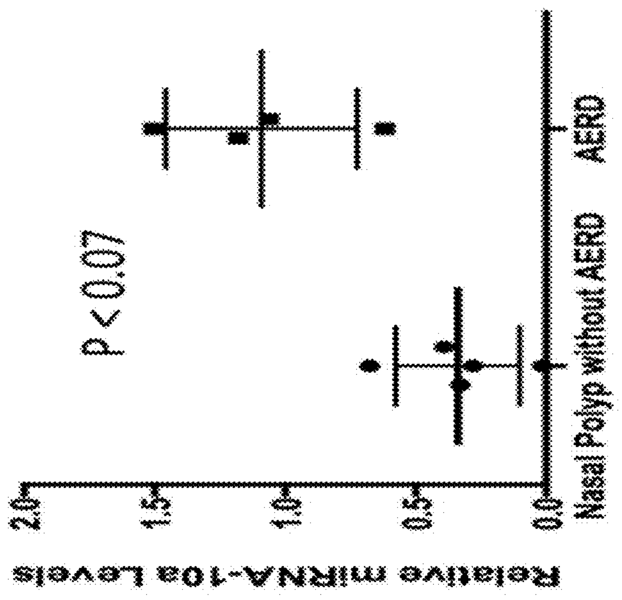

FIGS. 7A and 7B show the differential expression of nasal miRNAs (miRNA-1971 (FIG. 7A) and miRNA-10a (FIG. 7B)) between subjects having nasal polyps with or without AERD. These results confirms results obtained from a pooled PCR screening (Table 3)

Figure 8:
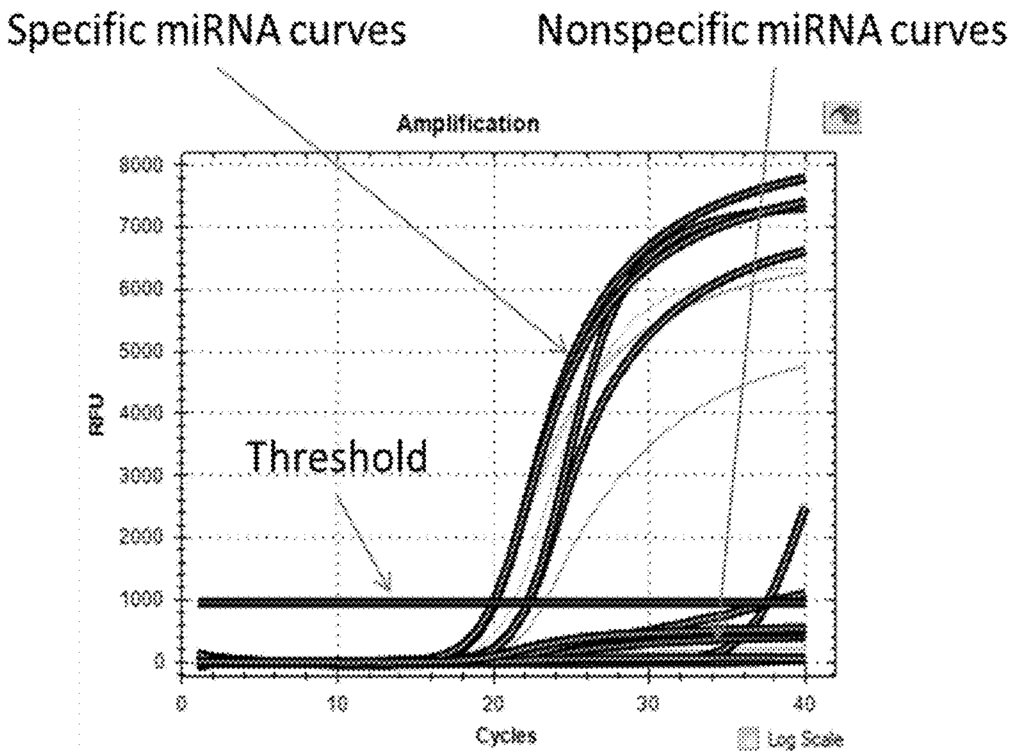
FIG. 8 demonstrates the amplification curves of the qPCR assay performed demonstrating high specificity of the isolation of miRNA via a target-specific pull-down assay. It also shows the amplification plot of synthetic miRNAs and demonstrates the specificity of the multiplexed real-time PCR assay described herein.

FIG. 8 demonstrates the amplification curves of the qPCR assay performed demonstrating high specificity of the isolation of miRNA via a target-specific pull down assay. Thick lines represent samples detected with VIC oligo-probes. Thin lines represent samples detected with FAM oligo probes.

Figure 9:
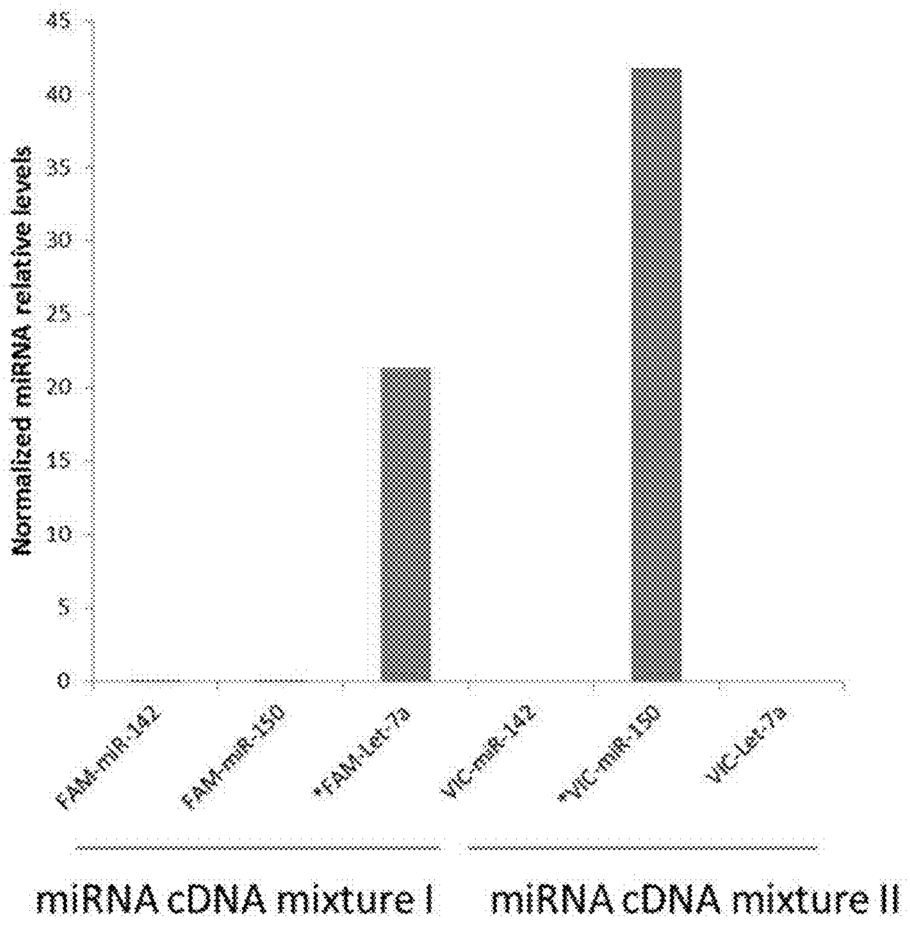
FIG. 9 demonstrates the results of the qPCR assay performed on the mixtures of synthetic miRNAs. The * indicates the miRNAs that were pulled downed specifically with their corresponding DNA oligos labeled with biotin. As shown, the assay is highly specific for a given target.

FIG. 9 demonstrates the results of the qPCR assay performed on the mixtures of synthetic miRNAs. The * indicates the miRNAs that were pulled downed specifically with their corresponding DNA oligos labeled with biotin. As shown, the assay is highly specific for a given target.

Table 3 demonstrates the results from a dual color real-time quantitative PCR (RT-qPCR) miRNA assays of pathogenic samples. Total RNAs were extracted from nasal cells collected from 10 subjects with nasal polyps and AERD as AERD pooled group, 10 subjects with nasal polyps and without AERD as nasal polyps and without AERD pooled group. The miRNAs from the two pooled RNA samples were polyadenylated and then reversely transcribed with two universal RT primers with different probe binding sites. Equal amount of cDNAs were mixed together and detected by qPCR with a FAM probe and a VIC probe for each miRNA in the same PCR well with a 96 well plate format. Data were represented as the values normalized to the average.

TABLE 3

| miRNA | No AERD | AERD | miRNA | No AERD | AERD | miRNA | No AERD | AERD |
|---|---|---|---|---|---|---|---|---|
| mmu-let-7a | 0.45 | 0.30 | mmu-miR-3093-5p | 0.45 | 0.30 | mmu-miR-434-5p | 0.45 | 0.30 |
| mmu-let-7b | 0.45 | 0.30 | mmu-miR-15b | 0.51 | 0.43 | mmu-miR-449a | 0.45 | 0.30 |
| mmu-let-7e | 0.45 | 0.30 | mmu-miR-195 | 0.45 | 0.30 | mmu-miR-34b-5p | 0.45 | 0.30 |
| mmu-let-7g | 0.45 | 0.30 | mmu-miR-181c | 0.45 | 0.30 | mmu-miR-374 | 0.45 | 0.30 |
| mmu-miR-1961 | 4.69 | 6.83 | mmu-miR-193 | 0.45 | 0.30 | mmu-miR-376b | 0.45 | 0.30 |
| mmu-miR-669h-5p | 0.45 | 0.45 | mmu-miR-1931 | 0.82 | 0.63 | mmu-miR-412-3p | 0.45 | 1.04 |
| mmu-miR-1-2-as-3p | 0.45 | 0.30 | mmu-miR-1935 | 2117.47 | 3287.35 | mmu-miR-455 | 0.45 | 0.30 |
| mmu-miR-100 | 0.45 | 0.30 | mmu-miR-485 | 0.45 | 0.30 | mmu-miR-669i | 87.92 | 142.29 |
| mmu-miR-10a | 1.12 | 3.12 | mmu-miR-1937a | 753.85 | 5158.40 | mmu-miR-568 | 0.45 | 0.30 |
| mmu-miR-101b | 4.88 | 4.09 | mmu-miR-1937c/200 | 1507.69 | 11057.28 | mmu-miR-489 | 1.24 | 1.59 |
| mmu-miR-103 | 0.45 | 0.35 | mmu-miR-1946b | 2.92 | 17.06 | mmu-miR-500 | 1.23 | 1.77 |
| mmu-miR-106a | 0.45 | 0.30 | mmu-miR-743b-5p | 0.45 | 0.48 | mmu-miR-883a-3p | 0.45 | 0.30 |

TABLE 3-continued

| miRNA | No AERD | AERD | miRNA | No AERD | AERD | miRNA | No AERD | AERD |
|---|---|---|---|---|---|---|---|---|
| mmu-miR-3082-5p | 1.37 | 1.63 | mmu-miR-3067 | 0.45 | 0.30 | mmu-miR-105 | 0.45 | 0.30 |
| mmu-miR-466h-5p | 13.91 | 15.81 | mmu-miR-882 | 0.45 | 0.80 | mmu-miR-1190 | 0.45 | 0.30 |
| mmu-miR-466f-5p | 0.45 | 0.30 | mmu-miR-196a | 0.68 | 0.70 | mmu-miR-1193-3p | 0.45 | 1.95 |
| mmu-miR-669d | 0.45 | 0.30 | mmu-miR-1971 | 5.31 | 12.58 | mmu-miR-1194 | 0.45 | 0.87 |
| mmu-miR-6690-5p | 0.45 | 0.30 | mmu-miR-423-3p | 0.45 | 2.07 | mmu-miR-1197 | 0.64 | 3.93 |
| mmu-miR-466d-5p | 0.45 | 0.30 | mmu-miR-26b | 0.45 | 0.30 | mmu-miR-1199 | 0.45 | 1.78 |
| mmu-miR-669a-5p | 0.45 | 0.30 | mmu-miR-27b | 2.34 | 0.42 | mmu-miR-124 | 0.45 | 1.12 |
| mmu-miR-3097-5p | 1.71 | 2.45 | mmu-miR-292-3p | 0.45 | 0.30 | mmu-miR-1249 | 6.36 | 10.01 |
| mmu-miR-670 | 67.56 | 69.20 | mmu-miR-292-5p | 0.45 | 0.36 | mmu-miR-153 | 0.45 | 0.30 |
| mmu-miR-294 | 0.45 | 0.30 | mmu-miR-302d | 0.45 | 0.30 | mmu-miR-155 | 0.45 | 0.58 |
| mmu-miR-468 | 0.45 | 0.30 | mmu-miR-302c | 0.45 | 0.30 | mmu-miR-182 | 0.45 | 0.30 |
| mmu-miR-495 | 0.45 | 0.30 | mmu-miR-291a-5p | 0.45 | 0.30 | mmu-miR-1839-5p | 0.45 | 0.30 |
| mmu-miR-133b | 1.21 | 1.09 | mmu-miR-29a | 0.45 | 0.30 | mmu-miR-1843-3p | 1.75 | 1.98 |
| mmu-miR-380-5p | 0.45 | 0.48 | mmu-miR-29b | 0.45 | 0.30 | mmu-miR-185 | 0.45 | 0.46 |
| mmu-miR-135b | 0.45 | 0.30 | mmu-miR-3070b-3p | 13.34 | 18.41 | mmu-miR-187 | 1.67 | 2.13 |
| mmu-miR-200a | 0.45 | 0.30 | mmu-miR-3074-2-3p | 0.54 | 0.60 | mmu-miR-188-5p | 5.57 | 9.34 |
| mmu-miR-146a | 0.45 | 0.30 | mmu-miR-344b | 0.45 | 0.30 | mmu-miR-1895 | 20.23 | 32.06 |
| mmu-miR-148a | 0.45 | 0.30 | mmu-miR-344c | 28.80 | 38.13 | mmu-miR-1897-3p | 0.45 | 0.54 |
| mmu-miR-152 | 0.45 | 0.30 | mmu-miR-344g-3p | 0.45 | 0.41 | mmu-miR-1898 | 0.45 | 0.30 |
| mmu-miR-28 | 0.45 | 0.30 | mmu-miR-3470b | 0.45 | 0.81 | mmu-miR-1901 | 0.78 | 1.40 |

We claim:

1. A method comprising:

contacting a sample containing a first RNA molecule with an effective amount of poly(A)polymerase to produce a first 3' end-polyadenylated RNA molecule;

contacting the first 3' end-polyadenylated RNA molecule with an effective amount of a first reverse-transcription (RT) stem-loop reverse primer and an effective amount of a reverse-transcriptase to produce a first cDNA molecule, where the first reverse-transcription (RT) stem-loop reverse primer comprises:

an oligo dT sequence having a 5' and a 3' end, the oligo dT sequence being flanked on the 5' end by a stem-loop adapter sequence, and where the stem-loop adapter sequence contains a first oligo-probe specific sequence that hybridizes with a first oligo-probe;

contacting a sample containing a second RNA molecule with an effective amount of poly(A)polymerase to produce a second 3' end-polyadenylated RNA molecule;

contacting the second 3' end-polyadenylated RNA molecule with an effective amount of a second reverse-transcription (RT) stem-loop reverse primer and an effective amount of a reverse-transcriptase to produce a second cDNA molecule, where the second reverse-transcription (RT) stem-loop reverse primer comprises:

an oligo dT sequence having a 5' and a 3' end, the oligo dT sequence being flanked on the 5' end by a stem-loop adapter sequence, and where the stem-loop adapter sequence contains a second oligo-probe specific sequence that hybridizes with a second oligo-probe;

contacting the first cDNA molecule with a first target-specific oligo bound to a molecular tag to form a first blocked cDNA molecule;

contacting the first blocked cDNA with a magnetic bead bound to a molecular substrate, wherein the molecular substrate is configured to specifically bind the molecular tag;

contacting the second cDNA molecule with a second target-specific oligo bound to a molecular tag to form a second blocked cDNA molecule;

contacting the second blocked cDNA with a magnetic bead bound to a molecular substrate, wherein the molecular substrate is configured to specifically bind the molecular tag;

exposing the first blocked cDNA to a magnetic field, exposing the second blocked cDNA to a magnetic field, combining the first cDNA molecule and the second cDNA molecule to form a multiplexed cDNA sample and wherein exposing the first blocked cDNA and the second blocked cDNA to a magnetic field occurs prior to the step of combining the first cDNA molecule and the second cDNA molecule, simultaneously contacting the multiplexed cDNA sample with a first oligo-probe, a second oligo-probe, a first target-specific forward primer, a second target-specific forward primer, and a DNA polymerase, where the first target-specific forward primer and the second target-specific forward primer each have a melting temperature of within ±2° C. of a target melting temperature.

2. The method of claim 1, further comprising:

contacting a sample containing a third RNA molecule with an effective amount of poly(A)polymerase to produce a third 3' end-polyadenylated RNA molecule;

contacting the third 3' end-polyadenylated RNA molecule with an effective amount of a third RT stem-loop reverse primer and an effective amount of a reverse-transcriptase to produce a third cDNA molecule, where the third RT stem-loop reverse primer comprises:

an oligo dT sequence having a 5' and a 3' end, the oligo dT sequence being flanked on the 5' end by a stem-loop adapter sequence, and where the stem-loop adapter sequence contains a third oligo-probe specific sequence that hybridizes with a third oligo-probe;

wherein the step of combining the first cDNA molecule and the second cDNA molecule further comprises combining the third cDNA molecule to form the multiplexed cDNA; and wherein the step of simultaneously contacting the multiplexed cDNA with the first oligo-probe, the second oligo-probe, the first target-specific forward primer, the second target-specific forward primer, and the DNA polymerase further comprises simultaneously contacting the multiplexed cDNA with a third oligo-probe and a third target-specific primer, wherein the third target-specific forward primer also has a melting temperature within ±2° C. of the target melting temperature.

3. The method of claim 2, further comprising:

contacting a sample containing a fourth RNA molecule with an effective amount of poly(A)polymerase to produce a fourth 3' end-polyadenylated RNA molecule;

contacting the fourth 3' end-polyadenylated RNA molecule with an effective amount of a fourth RT stem-loop reverse primer and an effective amount of a reverse-transcriptase to produce a fourth cDNA molecule, where the fourth RT stem-loop reverse primer comprises:

an oligo dT sequence having a 5' and a 3' end, the oligo dT sequence being flanked on the 5' end by a stem-loop adapter sequences, and where the stem-loop adapter sequence contains a fourth oligo-probe specific sequence that hybridizes with a fourth oligo-probe;

wherein the step of combining the first cDNA molecule, the second cDNA, and the third cDNA molecule further comprises combining the fourth cDNA molecule to form the multiplexed cDNA; and wherein the step of simultaneously contacting the multiplexed cDNA with the first oligo-probe, the second oligo-probe, the third oligo-probe, the first target-specific forward primer, the second target-specific, the third target-specific forward primer, and the DNA polymerase further comprises simultaneously contacting the multiplexed cDNA with a fourth oligo-probe and a fourth target-specific primer, wherein the fourth target specific forward primer each have a melting temperature of 70±1° C.

4. The method of any one of claims 1-3, wherein the target melting temperature is about 65° C.-75° C.

5. The method of claim 1, wherein the first RNA molecule is a messenger RNA molecule or a micro RNA molecule.

6. The method of claim 1, wherein the second RNA molecule is a messenger RNA molecule or a micro RNA molecule.

7. The method of claim 2, wherein the third RNA molecule is a messenger RNA molecule or a micro RNA molecule.

8. The method of claim 3, wherein the fourth RNA molecule messenger RNA molecule or a micro RNA molecule.

9. The method of claim 1, wherein the first target-specific forward primer, the second target-specific forward primer, the third target specific forward primer, and the fourth target specific forward primer have a GC content of about 29 percent to about 78 percent.

10. The method of claim 2, further comprising contacting the third cDNA molecule with a third target-specific oligo bound to a molecular tag to form a third blocked cDNA molecule;

contacting the second blocked cDNA with a magnetic bead bound to a molecular substrate, wherein the molecular substrate is configured to specifically bind the molecular tag; and exposing the third blocked cDNA to magnetic field, wherein exposing the third blocked cDNA to the magnetic field occurs before combining the first cDNA, second cDNA and third cDNA.

11. The method of claim 3, further comprising further comprising contacting the fourth cDNA molecule with a fourth target-specific oligo bound to a molecular tag to form a fourth blocked cDNA molecule;

contacting the fourth blocked cDNA with a magnetic bead bound to a molecular substrate, wherein the molecular substrate is configured to specifically bind the molecular tag; and exposing the fourth blocked cDNA to magnetic field, wherein exposing the fourth blocked cDNA to the magnetic field occurs before combining the first cDNA, second cDNA third cDNA, and fourth cDNA.

* * * * *